US010428086B2

(12) United States Patent
Viscomi et al.

(10) Patent No.: US 10,428,086 B2
(45) Date of Patent: *Oct. 1, 2019

(54) SOLVATED CRYSTAL FORM OF RIFAXIMIN, PRODUCTION, COMPOSITIONS AND USES THEREOF

(71) Applicant: ALFASIGMA S.p.A., Bologna (IT)

(72) Inventors: Giuseppe Claudio Viscomi, Bologna (IT); Paola Maffei, Bologna (IT); Annalisa Sforzini, Bologna (IT); Fabrizia Grepioni, Bologna (IT); Laura Chelazzi, Sesto Fiorentino (IT)

(73) Assignee: ALFASIGMA S.P.A., Bologna (IT)

( * ) Notice: Subject to any disclaimer, the term of this patent is extended or adjusted under 35 U.S.C. 154(b) by 0 days.

This patent is subject to a terminal disclaimer.

(21) Appl. No.: 15/907,117

(22) Filed: Feb. 27, 2018

(65) Prior Publication Data

US 2018/0354971 A1 Dec. 13, 2018

Related U.S. Application Data

(63) Continuation of application No. 15/310,436, filed as application No. PCT/IB2015/053342 on May 7, 2015, now Pat. No. 9,938,298.

(60) Provisional application No. 61/992,017, filed on May 12, 2014.

(51) Int. Cl.
    *C07D 498/22* (2006.01)

(52) U.S. Cl.
    CPC ........ *C07D 498/22* (2013.01); *C07B 2200/13* (2013.01)

(58) Field of Classification Search
    CPC .................................................. C07D 498/22
    See application file for complete search history.

(56) References Cited

U.S. PATENT DOCUMENTS

| 4,341,785 A | 7/1982 | Marchi et al. |
| 4,557,866 A | 12/1985 | Cannata et al. |
| 5,356,625 A | 10/1994 | Ying |
| 5,443,826 A | 8/1995 | Borody |
| 5,840,332 A | 11/1998 | Lerner et al. |
| 6,861,053 B1 | 3/2005 | Lin et al. |
| 7,045,620 B2 | 5/2006 | Viscomi et al. |
| 7,452,857 B2 | 11/2008 | Lin et al. |
| 7,605,240 B2 | 10/2009 | Lin et al. |
| 7,612,199 B2 | 11/2009 | Viscomi et al. |
| 7,709,634 B2 | 5/2010 | Kothakonda et al. |
| 7,718,608 B2 | 5/2010 | Lin et al. |
| 7,902,206 B2 | 3/2011 | Viscomi et al. |
| 7,906,542 B2 | 3/2011 | Viscomi et al. |
| 7,915,275 B2 | 3/2011 | Viscomi et al. |
| 7,923,553 B2 | 4/2011 | Viscomi et al. |
| 7,928,115 B2 | 4/2011 | Forbes et al. |
| 7,935,799 B2 | 5/2011 | Lin et al. |
| 8,158,644 B2 | 4/2012 | Viscomi et al. |
| 8,158,781 B2 | 4/2012 | Viscomi et al. |
| 8,173,801 B2 | 5/2012 | Viscomi et al. |
| 8,193,196 B2 | 6/2012 | Viscomi et al. |
| 8,227,482 B1 | 7/2012 | Parent et al. |
| 8,309,569 B2 | 11/2012 | Forbes et al. |
| 8,404,704 B2 | 3/2013 | Viscomi et al. |
| 8,486,956 B2 | 7/2013 | Gushurst et al. |
| 8,507,517 B2 | 8/2013 | Parent et al. |
| 8,513,275 B2 | 8/2013 | Wu et al. |
| 8,518,949 B2 | 8/2013 | Viscomi et al. |
| 8,569,326 B2 | 10/2013 | Gushurst et al. |
| 8,633,234 B2 | 1/2014 | Rao et al. |
| 8,642,573 B2 | 2/2014 | Forbes et al. |
| 8,735,419 B2 | 5/2014 | Parent et al. |
| 8,741,904 B2 | 6/2014 | Viscomi et al. |
| 8,815,888 B2 | 8/2014 | Wu et al. |
| 8,829,017 B2 | 9/2014 | Forbes et al. |
| 8,835,452 B2 | 9/2014 | Viscomi et al. |
| 8,853,231 B2 | 10/2014 | Viscomi et al. |
| 8,877,770 B2 | 11/2014 | Vigano' et al. |
| 8,883,795 B2 | 11/2014 | Kothakonda et al. |
| 8,946,252 B2 | 2/2015 | Forbes et al. |
| 8,952,159 B2 | 2/2015 | Lavagna et al. |
| 8,969,398 B2 | 3/2015 | Forbes |
| 9,018,225 B1 | 4/2015 | Holha |
| 9,034,892 B2 | 5/2015 | Gushurst et al. |
| 9,133,217 B2 | 9/2015 | Parent et al. |
| 9,186,355 B2 | 11/2015 | Hotha |
| 9,273,066 B2 | 3/2016 | Gushurst et al. |
| 9,359,374 B2 | 6/2016 | Blazecka et al. |
| 9,421,195 B2 | 8/2016 | Forbes et al. |

(Continued)

FOREIGN PATENT DOCUMENTS

| CA | 1215976 A | 12/1986 |
| CA | 1218650 A | 3/1987 |

(Continued)

OTHER PUBLICATIONS

Byrn S. et al., "Pharmaceutical solids: a strategic approach to regulatory considerations", Pharmaceutical research, 1995, 12(7), pp. 945-954.
European Pharmacopoeia 7.0, Dissolution test for solid dosage forms, Jan. 2010, 256-263. 8 pages.
European Pharmacopoeia ED 8.0, Dissolution test for solid dosage forms, Jan. 2014, 288-295. 8 pages.
Nullity action concerning the German part No. DE 60 2004 006 367 T2 of European Patent No. EP 1 557 421 B1 Apr. 9, 2015. 43 pages (English Translation+ German Original).
Response to Nullity action concerning the German part No. DE 60 2004 006 367 T2 of European Patent No. EP 1 557 421 B1. Nov. 16, 2015. 91 pages (English Translation + German Original).

(Continued)

*Primary Examiner* — Bruck Kifle
(74) *Attorney, Agent, or Firm* — Lucas & Mercanti, LLP

(57) ABSTRACT

The present invention describes a new crystalline form of rifaximin, characterized in that it is a solvated form of rifaximin called rifaximin τ
The invention also describes a process for the preparation of rifaximin τ, a pharmaceutical composition comprising said rifaximin form, and its use for treating inflammations and infections.

3 Claims, 2 Drawing Sheets

(56) References Cited

U.S. PATENT DOCUMENTS

| | | |
|---|---|---|
| 9,629,828 B2 | 4/2017 | Forbes et al. |
| 9,708,343 B2 | 7/2017 | Vigano' et al. |
| 9,988,398 B2 | 6/2018 | Singh et al. |
| 2002/0107200 A1 | 8/2002 | Chang et al. |
| 2003/0059471 A1 | 3/2003 | Compton et al. |
| 2003/0157174 A1 | 8/2003 | Tsukuda et al. |
| 2004/0234601 A1 | 11/2004 | Legrand |
| 2005/0196418 A1 | 9/2005 | Yu et al. |
| 2005/0272754 A1 | 12/2005 | Viscomi et al. |
| 2008/0262024 A1 | 10/2008 | Viscomi et al. |
| 2009/0028940 A1 | 1/2009 | Lupin Ltd |
| 2011/0086871 A1 | 4/2011 | Viscomi et al. |
| 2012/0035202 A1 | 2/2012 | Viscomi et al. |
| 2012/0077835 A1 | 3/2012 | Selbo et al. |
| 2012/0202989 A1 | 8/2012 | Viscomi et al. |
| 2012/0203000 A1 | 8/2012 | Viscomi et al. |
| 2012/0214989 A1 | 8/2012 | Viscomi et al. |
| 2012/0245192 A1 | 9/2012 | Viscomi et al. |
| 2012/0258166 A1 | 10/2012 | Viscomi et al. |
| 2013/0028971 A1 | 1/2013 | Viscomi et al. |
| 2013/0281697 A1 | 10/2013 | Viscomi et al. |
| 2013/0289269 A1 | 10/2013 | Viscomi et al. |
| 2013/0310410 A1 | 11/2013 | Viscomi et al. |
| 2014/0079783 A1 | 3/2014 | Viscomi et al. |
| 2014/0308350 A1 | 10/2014 | Viscomi et al. |
| 2015/0073007 A1 | 3/2015 | Viscomi et al. |
| 2015/0080421 A1 | 3/2015 | Viscomi et al. |
| 2015/0175627 A1 | 6/2015 | Viscomi et al. |
| 2015/0182508 A1 | 7/2015 | Viscomi et al. |
| 2016/0362419 A1 | 12/2016 | Viscomi et al. |
| 2017/0071916 A1 | 3/2017 | Viscomi et al. |
| 2017/0210757 A1 | 7/2017 | Viscomi et al. |
| 2017/0210758 A1 | 7/2017 | Viscomi et al. |
| 2018/0065987 A1 | 3/2018 | Viscomi et al. |
| 2018/0065988 A1 | 3/2018 | Viscomi et al. |
| 2018/0291032 A1 | 10/2018 | Viscomi et al. |
| 2018/0354971 A1 | 12/2018 | Viscomi et al. |

FOREIGN PATENT DOCUMENTS

| | | |
|---|---|---|
| DE | 602004006367 | 9/2007 |
| EP | 1317830 A | 5/1973 |
| EP | 0161534 A2 | 11/1985 |
| EP | 0547294 B1 | 6/1993 |
| EP | 0616808 B1 | 9/1996 |
| EP | 935417 B1 | 8/1999 |
| EP | 0858804 B1 | 6/2002 |
| EP | 1557421 A1 | 3/2004 |
| EP | 2210893 A1 | 11/2004 |
| EP | 1676847 A1 | 7/2006 |
| EP | 1698630 A1 | 9/2006 |
| EP | 1874273 B1 | 1/2008 |
| EP | 2059232 B1 | 3/2008 |
| EP | 1676847 B1 | 1/2009 |
| EP | 1676848 B1 | 1/2009 |
| EP | 2011486 A1 | 1/2009 |
| EP | 2208730 A1 | 7/2010 |
| EP | 2420226 A1 | 2/2012 |
| EP | 2927235 A1 | 10/2015 |
| EP | 3126367 A1 | 2/2017 |
| EP | 2059232 B1 | 4/2017 |
| EP | 2618819 B1 | 11/2017 |
| GB | 2079270 A | 1/1982 |
| IT | 1154655 B | 1/1987 |
| IT | BO2005A000123 A1 | 9/2006 |
| IT | MI2005A000345 | 9/2006 |
| IT | MI2006A001692 A1 | 3/2008 |
| JP | 2013184902 A | 9/2013 |
| NZ | 531622 A | 3/2004 |
| WO | 2005/044823 A2 | 5/2005 |
| WO | 2006/0085812 A2 | 1/2006 |
| WO | 2006/094143 A2 | 9/2006 |
| WO | 2006/094144 A2 | 9/2006 |
| WO | 2006/094181 A2 | 9/2006 |
| WO | 2006/094662 A1 | 9/2006 |
| WO | 2006/094737 A2 | 9/2006 |
| WO | 2008/029208 A1 | 3/2008 |
| WO | 2008/035109 A1 | 3/2008 |
| WO | 2008/155728 A1 | 12/2008 |
| WO | 2009/008005 A1 | 1/2009 |
| WO | 2009/008005 A2 | 1/2009 |
| WO | 2009/047801 A1 | 4/2009 |
| WO | 2009/108730 A2 | 9/2009 |
| WO | 2010/044093 A1 | 4/2010 |
| WO | 2010/067072 A1 | 6/2010 |
| WO | 2011/050397 A1 | 5/2011 |
| WO | 2011/061519 A2 | 5/2011 |
| WO | 2011/061748 A1 | 5/2011 |
| WO | 2011/080691 A1 | 7/2011 |
| WO | 2011/088688 A1 | 7/2011 |
| WO | 2011/103120 A1 | 8/2011 |
| WO | 2011/110930 A2 | 9/2011 |
| WO | 2011/153444 A1 | 12/2011 |
| WO | 2011/156897 A2 | 12/2011 |
| WO | 2012/009387 A1 | 1/2012 |
| WO | 2012/009388 A1 | 1/2012 |
| WO | 2012/035283 A1 | 3/2012 |
| WO | 2012/038898 A1 | 3/2012 |
| WO | 2012/060675 A1 | 5/2012 |
| WO | 2012/076832 A1 | 6/2012 |
| WO | 2012/109605 A2 | 8/2012 |
| WO | 2012/150561 A1 | 11/2012 |
| WO | 2012/155981 A1 | 11/2012 |
| WO | 2012/156533 A1 | 11/2012 |
| WO | 2012/156951 A1 | 11/2012 |
| WO | 2013/185211 A1 | 12/2013 |
| WO | 2014/091432 A1 | 6/2014 |
| WO | 2014/186675 A1 | 11/2014 |
| WO | 2015/014984 A1 | 2/2015 |
| WO | 2011/051971 A2 | 5/2015 |
| WO | 2015/150171 A1 | 10/2015 |
| WO | 2015/159275 A2 | 10/2015 |
| WO | 2015/173697 A1 | 11/2015 |
| WO | 2016/063289 A2 | 4/2016 |
| WO | 2017/021975 A1 | 2/2017 |
| WO | 2011/061516 A2 | 9/2017 |
| WO | 2017/162725 A1 | 9/2017 |
| WO | 2017/162726 A1 | 9/2017 |
| WO | 2018/158646 A1 | 9/2018 |
| WO | 2018/178777 A1 | 10/2018 |
| WO | 2018/197538 A1 | 11/2018 |

OTHER PUBLICATIONS

Reply to response to nullity action of German counterpart of EP 1557421 B1. Feb. 8, 2016. 17 pages (English Translation+ German Original).

Submission filed by the Plaintiff on Feb. 23, 2016 with reference to nullity action of German validated counterpart of EP 1557421. 4 pages (English Translation + German Original).

Response filed by defendant on Apr. 1, 2016 with reference to nullity action of German counterpart EP 15577421 B1, 30 pages (English Translation+ German Original).

Response filed by Plaintiff on Apr. 4, 2016 with reference to nullity action of German counterpart EP 15577421 B1, 73 pages (English Translation+ German Original).

Response filed by Plaintiff on May 6, 2016 with reference to nullity action of German counterpart EP 15577421 B1, 11 pages (English Translation+ German Original).

Response filed by Defendant on May 11, 2016 with reference to nullity action of German counterpart EP 15577421 B1, 34 pages (English Translation+ German Original).

Response filed by Plaintiff on Jun. 16, 2016 with reference to nullity action of German counterpart EP 15577421 B1 9 pages (English Only).

Minutes of oral proceeding of Jun. 28, 2016 with reference to nullity action of German counterpart EP 15577421 B1. 6 pages (English Translation+ German Original).

Written decision of the court of Jun. 28, 2016 with reference to nullity action of German counterpart EP 15577421 B1. 96 pages (English Translation+ German Original).

(56) References Cited

OTHER PUBLICATIONS

Appeal brief concerning the nullity action of German part No. DE 60 2004 006 367 T2 of European Patent No. EP 1 557 421 B1. Dec. 15, 2016. 6 pages (English Translation+ German Original).

Appeal substantiation filed by the Plaintiff concerning the nullity action of German part No. DE 60 2004 006 367 T2 of European Patent No. EP 1 557 421 B1. Mar. 14, 2017. 115 pages (English Translation + German Original).

Response to the appeal substantiation filed by the Defendant concerning the nullity action of German part No. DE 60 2004 006 367 T2 of European Patent No. EP 1 557 421 B1. Jul. 13, 2017. 89 pages. (English Translation+ German Driginal).

Response to the summons to attend Oral Proceedings filed by the Opponent on Dec. 16, 2016 for the European Patent N. 1 698 630. 13 pages (English).

Response to the Opponent's letter filed by the Applicant on Jan. 26, 2017 for the European Patent N. 1 698 630. 7 pages (English).

Response to the Opponent's letter filed by the Applicant on Feb. 8, 2017 for the European Patent N. 1 698 630. 2 pages (English).

European Patent N. 1 698630, Opposition Proceedings, "Notice of opposition to the European Patent", Jun. 3, 2017. 14 pages (English).

Grounds for the decision of the Opposition Division about the opposition against EP 1 698 630, Mar. 6, 2015. 31 pages (English).

Notice of appeal concerning the Opposition against European Patent N. 1 698 630. Apr. 18, 2017. 2 pages (English).

Notice of termination of opposition proceedings against European Patent EP1557421. Mar. 6, 2013. 2 pages (English).

Burla, MC, et al. "// Milione: a suite of computer programs for crystal structure solution of proteins", J. Appl. Cryst, 2007, 40, 609-613.

European Commission, Health & Consumer Protection Directorate—General; Scientific Committee on Consumer Products [SCCP], Opinion on Diethylene Glycol Monoethyl ether [DEG EE], Dec. 19, 2006, 27 pgs.

Farrugia LJ, "WinGX and ORTEP for Windows: an update", J. Appl. Cryst., 2012, 45, 849-854.

International Search Report dated Jul. 16, 2015 for International Application PCT/IB2015/053342 filed on May 7, 2015 in the name of Alfa Wassermann S.P.A. 5 pages.

Lorenzetti, R. et al, "Rationale for the use of rifaximin in inflammatory bowel diseases based on clinical trial results", Clin. Invest, 2013, 3 (12), 1187-1193.

Written Opinion dated Jul. 16, 2015 for International Application PCT/IB2015/053342 filed on May 7, 2015 in the name of Alfa Wassermann S.P.A. 5 pages.

"Rifaximin" Merck Index, 13th Edition, Jan. 1, 2001, p. 1475.

"Rifamycins" Merck Index, 13th Edition, Jan. 1, 2001, p. 1474.

Braga, Dario et al., "The structure—property relationship of four crystal forms of rifaximin", CrystEngComm, vol. 14, No. 20, 2012, 6404-6411.

Macrae, CF, et al. "Mercury CSD 2.0—new features for the visualization and investigation of crystal structures", J. Appl. Crystallogr. 2008, 41, 466-4 70.

EP 1557421, Opposition Proceedings, "Notice of opposition to a European Patent" dated Feb. 11, 2008. 13 pages.

EP 1557421, Opposition Proceedings, "Patentee response to Notice of Opposition" dated Sep. 10, 2008. 21 pages.

EP 1557421, Opposition Proceedings, "Summons to attend oral proceedings" dated Jan. 19, 2009. 9 pages.

EP 1557421, Opposition Proceedings, "Patentee response to summons to attend oral proceedings" dated Apr. 22, 2009. 15 pages.

EP 1557421, Opposition Proceedings, "Opponent response to summons to attend oral proceedings" dated Jan. 23, 2009. 18 pages.

EP 1557421, Opposition Proceedings, "Patentee response to brief communication" Mail Date: May 29, 2009. 11 pages.

EP 1557421, Opposition Proceedings, "Opponent Response to the late submissions of patentee" Mail Date: Jun. 11, 2009. 3 pages.

EP 1557421, Opposition Proceedings, "EPO Decision rejecting the opposition" Mail Date: Jul. 8, 2009. 14 pages.

EP 1557421, Opposition Proceedings, "Appellant Notice of Appeal" Mail Date: Sep. 18, 2009. 4 pages.

EP 1557421, Opposition Proceedings, "Appellant Statement of Grounds for Appeal" Mail Date: Nov. 18, 2009. 18 pages.

EP 1557421, Opposition Proceedings, "Patentee Response to opponent statement setting out the grounds of appeal" Mail Date: Jun. 2, 2010. 29 pages.

Alivisi et al. Treatment of Secretory Diarrhoeas Clinical Trials Journal 1984, No. 4, pp. 215-223.

Rodriguez-Spong B. et al. "General Principles of pharmaceutical solid polymorphism: a supramolecular perspective" Advanced Drug Delivery Reviews 56 (2004), pp. 241-274.

Morris K R et al., Theoretical approaches to physical transformation s of active pharmaceutical ingredients during manufacturing processes Advanced Drug Delivery Reviews, 48, 2001, pp. 91-114.

Viscomi et al. "Crystal forms of rifaximin and their effect on pharmaceutical properties" CrystEngComm, 2008, 10, pp. 1074-1081.

Brufani et al. X-Ray Crystal Structure ..J. of Antibiotics, 1984, vol. 37, No. 12, pp. 1623-1627.

Soros et al. "Selection of rifampicin-resistant . . . " Clin. Microbiol. Infect. 1997, vol. 3, pp. 147-151.

Department of Health & Human Services, letter dated Nov. 16, 2007 Agenzia Italiana del Farmaco: Certificate of GMP Compliance of a Manufacturer. 3 pages.

European Medicines Industry: ICH—Topic Q 6 A, Specifications: Test Procedures and Acceptance Criteria for New Drug Substances and New Drug Products: Chemical Substances, May 2000, pp. 1-32.

Henwood et al. Drug Development and Industrial Pharmacy, 26(4), pp. 403-408 (2000) pp. 403-408.

Brittain: "Polymorphism in Pharmaceutical Solids" Drugs and the Pharmaceutical Sciences, 1999, vol. 95, Chapter 4, pp. 125-181.

Bacci A. et al. "Sampling rifamycin conformational variety" New J. Chem., 2008, 32, pp. 1725-1735.

Venturini "Pharmacokinetics of L/105, a New Rifamycin, in Rats and Dogs, after Oral Administration" Chemotherapy, 1983, vol. 29; pp. 1-3.

Pelizza G. et al. "Polymorphism of Rifampicin" Il Farmaco—Ed. Sc., 1977, vol. 32, No. 7, pp. 471-481.

Rao et al. "On-line 2D-LC-ESI/MS/MS determination of rifaximin in rat serum" Biomed. Chromatogr. 2009, 6 pages.

Descombe et al. "Pharmacokinetic Study of Rifaximin after oral administration in healthy volunteers", Ing. J. Clin. Pharm. Res. XIV(2), 1994; pp. 51-56.

Synthesis of rifaximin obtained according to examples 7 and 9 reported in European Patent EP0161534. May 13, 2010. 16 pages.

Cellai et al. "A study of structure-activity relationships in 4-deoxypyrido[1 ',2'-1,2] imidazo[5,4-c?rifamycin SV derivatives by electron spectroscopy for chemical analysis and H NMR" Molecular Pharmacology Sep. 25, 1984; vol. 27, pp. 103-108.

Consolidated list of references in the Opposition Proceedings against EP1698630. Prepared Feb. 7, 2017. 2 pages.

Summons to attend oral proceedings with reference to opposition of EP1698630 filed by Sandoz GmbH. Jul. 1, 2016. 9 pages.

Reply of the patent proprietor to the notice of opposition against EP 1 698 630, Mar. 23 2016. 28 pages.

Response to the summons to attend Oral Proceedings filed by the Applicant on Dec. 9, 2016 for the European Patent N. 1698630. 17 pages.

Declaration: Hotter "Preparation of raw rifaximin and of dried raw rifaximin according to Example 1 of EP1698630" May 29, 2015. 6 pages.

NORM IX Summary Product Characteristics, Jun. 1, 2000. 10 pages (Italian original + English translation).

NORMIX package 200 mg Sep. 2012, 8 pages.

NORMIX Package Insert 200 mg (Italian version) Oct. 2010, 13 pages.

Declaration Pichler "Analysis via Powder X-Ray Diffraction of Current NORMIX Tablets" May 29, 2015, 9 pages.

Declaration Dana Hoffmann: "Rifaximin: Oral Bioavailability Study in Dogs of four Different Polymorphic Isoforms" Jun. 3, 2015, 4 pages.

(56) References Cited

OTHER PUBLICATIONS

Caira "Crystalline Polymorphism of Organic Compounds" Topics in Current Chemistry, 1998, vol. 198, pp. 163-208.
Henck "Polymorphie von Arzneistoffen" Pharm .Ind. 59, Nr. 2, 1997, pp. 165-169.
EMEA, ICH Topic Q 6 A, "Test Prodecures and Acceptance Criteria for New Drug Substances" May 2000, 32 pages.
Experimental evidence filed by the applicant during the opposition against EP 1 698 630, Dec. 23, 2015, 13 pages.
Marzo, "Open Questions on Bioequivalence: Some Problems and Some Solutions" Pharmacological Research, 1999, vol. 40, No. 4, pp. 357-368.
Guidance Document: Conduct and Analysis of Comparative Bioavailability Studies, Health Canada Guidance for Industry, May 22, 2012, 46 pages.
Rifaximin Bioavailability Study in Dogs by the Oral Route, Final Report; RTC Study No. 33090EXT, Jan. 2005, 19 pages.
NORMIX Package Insert, Aug. 2009, 12 pages (Italian original+ English translation).
Karl Fischer titration, Wikipedia, retrieved from https://en.wikipedia.org/wiki/Karl Fischer titration on Mar. 15, 2016. 3 pages.
Otsuka et al. "Real-Time Monitoring of Changes of Adsorbed and crystalline Water Contents in Tablet Formulation Powder Containing Theophylline Anhydrate at Various Temperatures During Agitated Granulation by near-Infrared Spectroscopy" Journal of Pharmaceutical Sciences, 2014, vol. 103; pp. 2924-2936.
EMEA "Guideline on the Investigation of Bioequivalence", Jan. 20, 2010, 27 pages.
Shayto et al. "Use of rifaximin in gastrointestinal and liver diseases", WJG, Aug. 7, 2016; 22(29):6638-6651. 15 pages.
Appeal substantiation concerning the Opposition against European Patent N. 1 698 630. Jul. 6, 2017. 17 pages (English).
Nullity action against DE 60 2004 006 367 T2—Preliminary opinion of the Federal patent Court (German original), Mar. 4, 2016. 6 pages.
Appeal against decision of the Federal Patent Court on DE 60 2004 006 367 T2—Notice of oral proceedings, Jan. 18, 2018. 3 pages.
Appeal against decision of the Federal Patent Court on DE 60 2004 006 367 T2—Submission by Appellant (German original), Jun. 26, 2018. 30 pages.
Appeal against decision of the Federal Patent Court on DE 60 2004 006 367 T2—Minutes of the oral proceedings of Aug. 7, 2018. 16 pages.
Appeal against decision of the Federal Patent Court DE 60 2004 006 367 T2—Decision of the Federal Court of Justice. Dec. 11, 2018. 22 pages.
Appellee's test report D30 of the opposition appeal proceedings EP 1 698 630 filed with appeal substantiation of Jul. 6, 2017. 2 pages.
EP Register extract of EP 1557421 B1. Mar. 24, 2015. 4 pages.
German Patent and Trademark Office Register extract of DE 602004 006367 T2. Mar. 24, 2015. 2 pages.
Reasons for Decision by the European Opposition Division dated Jul. 8, 2009. 14 pages.
Medicinali Parte I, 2001: Rifacol®, p. 904-905 (Italian).
Australian Public Assessment Report for Rifaximin, Nov. 2012, pp. 1-11.
Xifaxan® (rifaximin) Tablets, 550 mg, NDA 22-554 "Briefing Document for Gastrointestinal Drug Advisory Committee Meeting" Meeting of Feb. 23, 2010 by the company Salix Pharmaceuticals, Inc., pp. 1-11, 22-23, 115-125.
Marzo A., A randomized, crossover study to evaluate the safety and the pharmacokinetic profilesof a single oral dose (400 mg) of amorphous rifaximin in comparison witha single oral dose of Normix® (Rifaximine polimorph a in healthy volunteers) Abstract p. 256, Digestive and Liver Disease 42S (2010) S 191-S 192.
Package insert of NORMIX® (Romanian), 2005. 30 pages.
Declaration by G.C. VISCOMI regarding U.S. Appl. No. 10/728,090 of Jan. 10, 2006. 12 pages.
Opinion by Prof. Griesser, et al. regarding the reworking of EP 0161534 A2. Feb. 10, 2015. 12 pages.

Additional experiments by Professor Griesser. Feb. 19, 2016. 6 pages.
Test report (Example 1 of TM13) and declaration by Andreas Hotter. May 4, 2016. 8 pages.
Bruckner R. et al., Praktikum Praparative Organische Chemie, Springer Spektrum 2009; pp. 60-61.
Henck J.O. et al., Polymorphie von Arzneistoffen. Pharm. Ind. 1997; 52: 165- 169.
Table of granted patents claiming priority of IT MI20032144. Dec. 2, 2015. 1 page.
Reply to the Communication pursuant to Art. 96(2) EPC for the European Patent Application No. 04 00 5541.0, May 2, 2006. 5 pages.
Bass N.M. et al., Rifaximin Treatment in Hepatic EncephalopathyNEJM 2010, 362, 1071-1081.
Clinical dossier of Xifaxan, module 3.2P.2.1-2.3 Formulation Development, Dec. 2, 2015. 2 pages.
Table of polymorphic forms of rifaximin, Dec. 2, 2015. 1 page.
Huang L.F. et al. Impact of solid state properties on developability assessment of drug candidates Adv Drug Del Rev, 2004, 56, 321-334.
Market authorization of Rifaximina Sandoz (Italian). Nov. 2010. 2 pages.
Summary of Product Characteristics (SmPC) of Rifaximin Sandoz (Italian), 2010. 7 pages.
Blandizzi C. et al., Is generic rifaximin still a poorly absorbed antibiotic? A comparison of branded and generic formulations in healthy volunteers.Pharm Res, 2014, 85, 39-44.
Armarego W. L. F., Perrin D.D. Purification of Laboratory Chemicals, 4th edition, 1996, p. 12.
Sucker H. et al., Pharmazeutische Technologie, Georg Thieme Verlag, 1991, pp. 145 to 149 and 244 to 247.
Haleblian J. et al., Review Article "Pharmaceutical Applications of Polymorphism", J. of Pharm. Sciences, 58, 8, 1969, pp. 911-929.
Additional arguments in a summarizing table (German original). Feb. 8, 2016. 6 pages.
Zhang G.G. et al., Phase transformation considerations during process development and manufacture of solid oral dosage forms, Advanced Drug Delivery Reviews2004; 56: 371-390.
Italian Gazette (Gazetta Uthciale Della Repubblica Italiana), 2005, n. 171, p. 155.
Moretti A. et al., Role of rifaximin in the treatment of colonic diverticular disease. Clin Ter 2012; 163 (1), 33-38 (articolo in italiano).
Rivista Società Italiana de Medicina Generale, N. 2, Sep. 2011, p. 40-54.
Merck-Index, 1996, p. 1415.
Ritschel, "Die Tablette", Editio Cantor Verlag, 2nd edition 2002, pp. 28, 584.
Request for correction of figures. Sep. 10, 2008. 4 pages.
ICH Harmonised Tripartite Guideline, Specifications: Test Procedures and Acceptance Criteria for New Drug Substances and New Drug P. 35 pages. Products: Chemical Substances, Q6A, Oct. 6, 1999. 35 pages.
Declaration by Prof. Grepioni, Dec. 12, 2011. 5 pages.
Declaration of UIBM of Apr. 27, 2018. 1 page.
Declaration of UIBM of May 9, 2018. 3 pages.
Request for correction of Table 1 of Italian Patent No. 1.375.471, Sep. 10, 2008. 10 pages.
Extract from the Register of UIBM concerning the Italian Patent Application No. B02005A000123. May 15, 2018. 4 pages.
European Patent N. 2059232, Opposition, Experimental report I. Nov. 21, 2018. 10 pages.
European Patent N. 2059232, Opposition, Experimental report II. Nov. 21, 2018. 14 pages.
CV Dr. Giuseppe Viscomi. Nov. 21, 2018. 8 pages.
European Patent N. 2059232, Opposition, Overlays of Figures of "Experimental report I". Jan. 16, 2019. 4 pages.
European Patent N. 2059232, Opposition, Overlays of Figures of "Experimental report II". Jan. 16, 2019. 1 page.
Observation by Third Parties Mar. 20, 2015.
Observation by Third Parties Jan. 19, 2016.
Observation by Third Parties May 2, 2016.

(56) References Cited

OTHER PUBLICATIONS

Observation by Third Parties Nov. 15, 2016.
Observation by Third Parties Nov. 21, 2016.
European Patent N. 2618819 B1, Opposition, Notice of opposition to a European Patent, Jul. 31, 2018. 5 pages.
European Patent N. 2618819 B1, Opposition, Grounds of Opposition, Jul. 31, 2018. 19 pages.
European Patent N. 2618819, Opposition, Reply of the Patentee, Dec. 21, 2018. 24 pages.
Consolidated List of References cited in the Opposition against EP 2618819 B1. Dec. 21, 2018. 1 page.
Prantera C. et al., Antibiotic treatment of Crohn's disease: results of a multicenter double blind, randomized, placebo-controlled trial with rifaximin. Aliment. Pharmacol. Ther., 2006, 23, 1117-1125.
Prantera C. et al.,Rifaximin-extended intestinal release induces remission in patients with moderately active Crohn's disease, Gastroenterology, 2012, 142, 473-481.
Palma-Aguirre J.A. et al., Bioavailability of two oral suspension and two oral tablet formulations of acyclovir 400 mg: Two single-dose, open-label, randomized, two-period crossover comparisons in healthy Mexican adult subjects, clinical therapeutics, 2007, 29.6: 1146-1152.
Bacchieri A. et al., Fundamentals of Clinical Research, Springer-Verlag Italia, Milano, 2004, pp. 318-319, 332-333.
International Conference on Harmonisation, ICH topic E9: Statistical principle for clinical trials. (1998). 39 pages.
Alfasigma S.p.A., Clinical study report, RETIC/03/06, Apr. 29, 2010, 5 pages.
Alfasigma S.p.A., Clinical study report, GRACE01. Apr. 2006, 4 pages.
European Patent No. 2927235, Opposition, Notice of opposition, Nov. 8, 2017. 44 pages.
European Patent No. 2927235, Opposition, Response to Notice of opposition Apr. 16, 2018. 44 pages.
European Patent No. 2927235, Opposition, Summons to attent Oral proceedings, Jul. 26, 2018. 13 pages.
European Patent No. 2927235, Opposition, Written submission by the Opponent, Dec. 13, 2018. 22 pages.
European Patent No. 2927235, Opposition, Written submission by the Patentee, Jan. 14, 2019. 5 pages.
Consolidated list of References in Opposition to No. 2 927 235 B1 (Euticals).Dec. 2018, 2018. 3 pages.
Summary of Product Characteristics of NORMIX (2009, Italy).
Targaxan: www.medicine.org.uk, Jan. 10, 2013.
Campbell R.S.N. et al.,Quantitative analysis of mannitol polymorphs. X-ray powder diffractometry—exploring preferred orientation effects. J. Pharm. Biomed. Anal. 2002; 28, 1149-1159.
Bobrovs R. et al., Optimization of sample preparation conditions for detecting trace amounts of β-tegafur in α- and β-tegafur mixture. J. Pharm. Sciences 2012; 101, 4608-4614.
Gibson M., Pharmaceutical Preformulation and Formulation", 2001, IHSHEALTH Group, article "Oral solid dosage forms, pp. 403-440.
Zevin L.S. et al., Quantitattive X-Ray Diffractometry , Ed. By I. Mureinik, Springer-Verlag, 1995, 5-7.
Jenkins R. et al., Introduction to X-ray Powder Diffractometry, Wiley & Sons Inc., 1996, 355-361.
Shankland K., in A. Muellertz et al. (eds.), Analytical Techniques in the Pharmaceutical Sciences,2016, Chapter 8, pp. 293-305.
Kidd et al. (1993). Powder Diffraction, 8(3), 180-187.
Characterization of crystalline and partially crystalline solids by X-ray powder diffraction (XRPD), U.S. Pharmacopeia 38th Ed. (2015), Reference No. 941, pp. 692 and 697, 2015.
Powder Diffraction. Theory and Practice. Edited by R. E. Dinnebier and S. J. L. Billinge. Cambridge: RSC Publishing, 2008. p. 125.
Alfa Wassermann Letter dated Sep. 10, 2008.
Dr. Sun Affidavit. Apr. 10, 2018.
Characterization of crystalline and partially crystalline solids by X-ray powder diffraction (XRPD), U.S. Pharmacopeia 35th Ed. (2012), Reference No. 941, pp. 427-433.

SYLOID® 244 FP Silica, Technical Data Sheet, Grace Davison Discovery Sciences, Apr. 2009, 2 pages.
Disodium Edetate, Handbook of Pharmaceutical Excipients 6th Ed.(2009), pp. 242-243.
Polyvinyl Alcohol, Handbook of Pharmaceutical Excipients 6th Ed.(2009), pp. 564-565.
ICH Harmonised Tripartite Guideline, Stability Testing of New Drug Substances and Products Q1A(R2), Current Step 4 version dated Feb. 6, 2003.
Declaration by Prof. Grepioni. Nov. 8, 2017.
Curriculum vitae Prof. Fabrizia Grepioni. Nov. 8, 2017.
Comparison of Figure 2 of WO 2009/108730 and Figure 2 of EP 2 927 235. Nov. 8, 2017.
Table corresponding to Annex 2 filed by Patentee on Apr. 6, 2016.
Table corresponding to Annex 2 filed by Patentee on Apr. 6, 2016, with alignment of peaks.
Curriculum vitae Dr. Viscomi. Dec. 13, 2018.
European Patent No. 1557421, Opposition, Withdrawal of the Appeal,. Feb. 5, 2013. 2 pages.
Consolidated List of Documents cited in the Opposition against EP 1557421 B1. Jun. 28, 2012. 4 pages.
EMEA European Medicines Industry: ICH—Topic Q 6 A, Specifications: Test Procedures and Acceptance Criteria for New Drug Substances and New Drug Products: Chemical Substances, May 2000, pp. 1-32.
*Civil Action* vs. *Actavis Laboratories FL, Inc.*, Notification of certifications of invalidity. Feb. 11, 2016. 110 pages.
*Civil Action* vs. *Actavis Laboratories FL, Inc.*, Proprietor's answer, defenses and counterclaims. May 24, 2016. 99 Pages.
*Civil Action* vs. *Actavis Laboratories FL, INC.*, Stipulated Consent Judgment and Injunction. Sep. 17, 2018. 4 pages.
*Civil Action* vs. *Actavis Laboratories FL, INC.*, Report to the Patent and Trademark Office. Sep. 17, 2018. 6 pages.
Corazza G.R. et al., Treatment of Small Intestine Bacterial Overgrowth with Rifaximin, a Non-absorbable Rifamycin, 1988. J. Int. Med. Res, 16: 312-316.
Husebye E., Gastrointestinal motility disorders and bacterial overgrowth, J. Intern. Med, 1995. 237: 419-427.
Peeters T.L. et al., Effect of Motilin on Gastric Emptying in Patients with Diabetic Gastroparesis, Gastroenterology, 1992. 102: 97-101.
Beseghi U. et al. Comparison of two non-absorbable antibiotics for treatment of bacterial enteritis in children, 1998. Eur Rev Med Pharmacol Sci, May 3-4, 1998, pp. 131-136.
Hardman et al., Chapter 1 Pharmacokinetics, Goodman & Gillman's The Pharmacological Basis of Therapeutics, McGraw-Hill, 10 Ed., Jan. 2001, pp. 15-17.
Scarpignato C. et al., Rifaximin, A Poorly Absorbed Antibiotic: Pharmacology and Clinical Use, edited by C. Scarpignato, Chemotherapy, 2005. 51 (Suppl. I) 36-66.
Sama C. et al., Clinical Effects of Rifaximin in Patients with Hepatic Encephalopathy Intolerant or Nonresponsive to Previous Lactulose Treatment: An Open-Label, Pilot Study, 2004, Curr. Ther. Res, 65: 413-422.
Puxeddu A. et al., Rifaximin in the treatment of chronic hepatic encephalopathy, Curr. Med. Res. Opin., 1995: 13: 274-281.
Adachi J.A. et al., Rifaximin: A Novel Nonabsorbed Rifamycin for Gastrointestinal Disorders, Clin. Infect. Diseases, 2006: 42: 541-547.
Lichtenstein G.R. et al. Rifaximin: Recent Advances in Gastroenterology and Hepatology, 2007; Gastroenterology and Hepatology, 3: 474-483.
Paik Y.H. et al., Comparison of Rifaximin and Lactulose for the Treatment of Hepatic Encephalopathy: A Prospective Randomized Study, 2005; Yonsei Med. J., 46: 399-407.
Shen B. et al., Oral Rifaximin as Maintenance Therapy for Antibiotic-Dependent Pouchitis, Amer. J. Gastroenterology, 2006: 101 (9), S441-42, 1130.
Durand F. et al., Assessment of the prognosis of cirrhosis: Child—Pugh versus MELD, J. Hepatology 2005, 42, S100-S107.
Sivapalasingam S., Rifaximin: A useful drug for travelers' diarrhea. Retrieved from <http://www.clinicalcorrelations.org/?p=475>, Clinical Correlations, NYU Langone Online J. of Med. Sep. 2007, 2 pages.

(56) References Cited

OTHER PUBLICATIONS

Pimentel M. et al., The Effect of a Nonabsorbed Oral Antibiotic (Rifaximin) on the Symptoms of the Irritable Bowel Syndrome, Ann. Intern, Med. 2006, 145: 557-563.
Study to Assess the Efficacy and Safety of Rifaximin Administered BID in the Treatment of Patients with Diarrhea-Associated Irritable Bowel Syndrome. Taken from <https://clinicaltrials.gov/ct2/show/study/NCT002694123>, US National Library of Medicine, Dec. 2005. 3 pages.
Nies A., Goodman & Gillman's The Pharmacological Basis of Therapeutics, Chapter 4 Principles of Therapeutics, 8th Ed., Pergamon Press, Jan. 1990, pp. 62-65 and 74-77 (8 pgs total).
Lipsky M.S. et al., From Idea to Market: The Drug Approval Process, J. Am. Board Fam. Med., 2001, 14: 362-367.
Expert Opinion of Prof. Rolf Daniels, filed by Plaintiff (German original). Apr. 1, 2016. 6 pages.
a) Committee for Proprietary Medicinal Products Emea Guideline CPMP/QWP/155/96, Jan. 28, 1998. 10 pages.
b) DSC Rifaximin according to Example 1 of TM13 without drying, filed by Plaintiff on Apr. 4, 2016. 1 page.
c) Loss by drying of Rifaximin form β, filed by Plaintiff on Apr. 4, 2016. 4 pages. (German original + English translation).
Rifampicin, Ph. Eur., 4.0, 2002, pp. 2804-2805, 2 pages.
Legislative Decree No. 178/1991 (Italian). 26 pages.
Commission Regulation (EC) No. 1084/2003 (German). Jun. 3, 2003. 24 pages.
Secondary change to the Marketing Authorization (Italian). Dec. 10, 2004. 1 page.
Xu Y. et al., Solid-State Characterization and Transformation of Various Creatine Phosphate Sodium Hydrates. J Pharm Sci. 2014, 103: 3688-95.
Gallo G.G. et al., Analytical profiles of drug substance, K. Florey academic press, 1976; 5; 467-489.
Rifaximin form alpha—Single crystal data. Electronic supplementary material of TM12. X-ray analysis. Jun. 24, 2016. 1 page.
Rifaximin, European pharmacopoeia 6.5, 2009, 4955-4957.
European Patent N. 1698630, Opposition, Written submission by the Opponent, Dec. 9, 2016. 11 pages.
European Patent N. 1698630, Opposition, Response by the Patentee, Jan. 26, 2017. 7 pages.
European Patent N. 1698630, Opposition, Response by the Opponent, Feb. 2, 2017. 1 page.
European Patent N. 1698630, Opposition, Statement of Grounds for Appeal by Appellant. Jul. 6, 2017. 17 pages.
European Patent N. 1698630, Opposition, Response of the Opponent, Nov. 30, 2017. 27 pages.
European Patent N. 1698630, Opposition, Response of the Appellant, Jan. 23, 2018. 18 pages.
Consolidated List of References Cited in the Opposition against EP 1698630 B1. Feb. 8, 2017.
Bernstein J. et al., Concomitant Polymorphs, Angew. Chem. Int. Ed. 1999, 38, pp. 3440-3461.
European Patent N. 1698630, Opposition, Experimental Report, Jul. 6, 2017. 2 pages.
European Patent N. 1698630, Opposition, Technical opinion by Professor Fabrizia Grepioni. Jul. 6, 2017. 5 pages.
Greenspan L. et al. Humidity fixed points of binary saturated aqueous solutions. Journal of research of the national bureau of standards, 1977, 81.1: pp. 89-96.
NORMIX® Package Insert 200 mg, Sep. 2012, (Italian original), 2 pages.
European Patent No. 1698630 B1, Opposition, Expert Statements of Dr. H. Gille, Bioavailability of rifaximin polymorphs in dogs, Dec. 1, 2016. 30 pages.
Minutes of the oral proceedings during the nullity proceedings against EP 1 557 421 on Jun. 28, 2016, 3 pages (documento in tedesco).
European Patent No. 1698630 B1, Opposition, Expert Statement of Dr. Gille, Bioavailability of Rifaximin Polymorphs in Dogs, Feb. 2, 2017. 5 pages.

European Patent N. 2059232 B1, Opposition, Summons to attend Oral Proceedings, Jul. 12, 2018. 9 pages.
European Patent N. 2059232 B1, Opposition, Grounds of opposition filed by Zaklady Farmaceutyczne Polpharma S.A. (Opponent 1). Jan. 17, 2018. 19 pages.
European Patent N. 2059232 B1, Opposition, Grounds of opposition filed by Sandoz GmbH (Opponent 2). Jan. 19, 2018. 23 pages.
European Patent N. 2059232 B1, Opposition, Grounds of opposition filed by Pentafarma Sociedade Tecnico-Medicinal S.A. (Opponent 3), Jan. 19, 2018. 25 pages.
European Patent N. 2059232 B1, Opposition, Response of the Patentee, Jun. 1, 2018. 36 pages.
European Patent N. 2059232 B1, Opposition, Response to the Summons to attend oral proceedings by Patentee, Nov. 21, 2018. 14 pages.
European Patent N. 2059232 B1, Opposition, Response by Opponent 2, Nov. 23, 2018. 9 pages.
European Patent N. 2059232 B1, Opposition, Response Brief of the Patentee Jan. 8, 2019. 4 pages.
European Patent N. 2059232 B1, Opposition, Response of Opponent 2, Jan. 16, 2019. 4 pages.
Consolidated List of References cited in the Opposition against EP 2059232 B1. Jan. 16, 2019. 3 pages.
Summary of Product Characteristics of Normix® in Italy from 1985.
Summary of Product Characteristics of Normix® in the Czech Republic in 2003. 3 pages.
Rowe R. C., et al., Handbook of pharmaceutical excipients. London: Pharmaceutical press, 5th Ed., 2006., p. 217-221.
Rifaximin, printout from Wikipedia, Jan. 18, 2018. 4 pages.
Cellulose, printout from Wikipedia, Jan. 18, 2018. 8 pages.
Figures 1 and 5 of the opposed patent with indication of polymorph α peaks according to TM1 (D13). Jan. 18, 2018. 2 pages.
Figure 4 of the opposed patent with indication of polymorph beta peaks according to TM1 (D13). Jan. 18, 2018. 2 pages.
European Patent No. EP 2 059 232, Opposition, Experimental report process according to claim 13 of EP2059323B1. Jan. 18, 2018. 4 pages.
Excerpt from European Patent Bulletin Feb. 2008. Jan. 9, 2008. 1 page.
Excerpt from European Patent Register EP 1 874 273. Jan. 16, 2018. 2 pages.
Excerpt from the Italian Patent Register of BO 2005 A 000123. May 15, 2018. 1 page.
Excerpt from the INPADOC patent family list of BO 2005 A 000123. Jan. 15, 2018. 1 page.
European Patent No. 2059232 B1, Opposition, Notice of Opposition, Feb. 7, 2018, 3 pages.
Richard Lynn, et al., Irritable Bowel Syndrome, The New England Journal of Medicine, vol. 329, No. 26, pp. 1940-1945, 1993.
European Pat No. 2059232—Minutes of Oral proceedings Apr. 4, 2019, 3 pages.
European Patent No. 2059232—Decision revoking patent Apr. 4, 2019, 18 pages.
European Patent No. 2927235, Opposition, New Summons to attend to Oral Proceedings Mar. 25, 2019, 16 pages.
Jiang, ZD et al. "In vitro activity and fecal concentration of rifaximin after oral administration", Antimicro Agent , Chemother 2000, vol. 44, pp. 2205-2206.
Hoover, WW et al. "Antimicrobial activity and spectrum of Rifaximin, a new topical Rifamycin derivative", Diag Microbiol Infect Dis, 1993, vol. 16, pp. 111-118.
Rossi et al., NMR Studies of a new class of Rifaximin-derived Molecules: Rifaximin OR (Open Ring), J. Chem Research (S) 1996, 268-269.
Seoul Central District Court 61st Civil Department Decision 2016 Gahap526938 Patent Infringement Injunction—Jul. 17, 2017. 15 pages.
KIPTAB Case No. 2015DANG5626—Feb. 17, 2006. 64 pages.
Sucker H. et al. Pharmazeutische Technologie, Georg Thieme Verlag, 191, pp. 145 to 149 and 244 to 247, (1991).

(56) References Cited

OTHER PUBLICATIONS

Bacchi A., et al. "Polymorphism-structure relationships of rifamexil, an antibiotic rifamycin derivative", Molecular Pharmacology, 1995, vol. 47, pp. 611-623.
Giron D., "Thermal analysis and calorimetric methods in the characterisation of polymorphs and solvates", Thermochimica Acta, 1995, 248, pp. 1-59.
Laird T., "Development and scale-up process for the manufacture of new pharmaceuticals in Comprehensive Medicinal Chemistry"—Pergamon Press, 1990, 1, pp. 321-359.
Miller S., Polymorphism-Interplay of Science and Regulation in SSCI—Pharmaceutical Solids May 13, 2005.
Beckmann W., "Seeding the desired polymorph background possibilities limitations and case studies", Org. Proc. Res. Dev. 2000, vol. 4, pp. 372-383.
Gionchetti P., et al., "Antibiotic combination therapy in patients with chronic, treatment-resistant pouchitis", Alimentary Pharmacology and Therapeutics, 1999; vol. 13, pp. 713-718.
Paik Y.H., et al., "Comparison of rifaximin and lactulose for the treatment of hepatic encephalopathy: a prospective randomized study", Yonsei Medical Journal, 2005, vol. 46, pp. 399-407.
Agenzia Italiana del Farmaco, Certificate of GMP Compliance of a Manufacturer, letter dated Feb. 3, 2010, 2 pages.
Notice of Allowance received for U.S. Appl. No. 11/814,628, dated Aug. 29, 2013, 12 pages.
Notice of Allowance received for U.S. Appl. No. 12/439,094, dated Feb. 17, 2012, 10 pages.
Notice of Allowance received for U.S. Appl. No. 13/544,945, dated Feb. 10, 2014, 8 pages.
S.Q. Henwood et al. "Characterization of the Solubility and Dissolution Properties of Several New Rifampicin Polymorphs, Solvates and Hydrates", Drug Dev. Ind. Pharm., vol. 27, No. 10, pp. 1017-1030, 2001.
Schwabe/Paffrath 2016, German+English translation, 4 pages.
SchwabelPaffrath 2015, German+English translation, 4 pages.
BPatGE, 20,6—Kristallformen (crystalline forms), German+English translation, 4 pages, (1977).

SOLVATED CRYSTAL FORM OF RIFAXIMIN, PRODUCTION, COMPOSITIONS AND USES THEREOF

CROSS REFERENCE TO RELATED APPLICATIONS

The present application is a continuation of U.S. application Ser. No. 15/310,436 filed on Nov. 10, 2016, which is the US national stage of International Patent Application PCT/IB2015/053342, filed on May 7, 2015, which, in turn, claims priority to U.S. Provisional Application No. 61/992,017 filed on May 12, 2014, all of which are incorporated by reference herein in their entirety, including any drawings.

BACKGROUND OF THE INVENTION

Rifaximin (INN, see The Merck Index, XIII ed., 8304, CAS No. 80621-81-4), IUPAC nomenclature (2S, 16Z, 18E, 20S, 21S, 22R, 23R, 24R, 25S, 26S, 27S, 28E)-5, 6, 21, 23, 25 pentahydroxy-27-methoxy-2, 4, 11, 16, 20, 22, 24, 26-octamethyl-2,7-(epoxypentadeca-(1,11,13)trienimino) benzofuro (4,5-e) pyrido (1,2,-a benzimidazole-1,15(2H) dione, 25-acetate) is a semi-synthetic antibiotic belonging to the class of rifampicins, more precisely it is a pyrido-imidazo rifamycin described in IT 1154655, whereas EP 0161534 describes a process for the production starting from rifamycin O (The Merck Index XIII ed., 8301).

Rifaximin is commercially available under the trademarks Normix®, Rifacol® and Xifaxan®. Rifaximin is an antibiotic that can be used locally with a broad spectrum of activity against Gram-positive and Gram-negative aerobic and anaerobic organisms. Rifaximin is characterized by low systemic absorption and is well known for its antibacterial effect on bacteria localized in the gastrointestinal tract, for example, *Escherichia coli* and *Clostridium difficile*. Rifaximin is also used for the treatment or prevention of intestinal disorders such as traveller's diarrhoea, infectious diarrhoea, and other diarrhoea irritable bowel syndrome, known as "irritable bowel disease" (IBS), bacterial overgrowth in the small intestine also known as "small intestinal bowel overgrowth" (SIBO), Crohn's disease (CD), colitis pancreatic insufficiency, enteritis, fibromyalgia, hepatic encephalopathy functional gastrointestinal disorder, functional dyspepsia with diarrhoea and other infections, for example, vaginal infections. Rifaximin is useful as antibacterial or prophylactic prior to and/or post colon surgery, and for dysentery, paucities, peptic ulcer disease, and bacterial dysbiosis.

Solid rifaximin can be in crystalline or in amorphous form. The crystalline forms can be polymorphic, hydrate, anhydrous or solvate forms and can have different solubility, and also different in vivo absorption.

Several patent applications describe polymorphic forms of rifaximin, for instance U.S. Pat. No. 7,045,620, US 2008/0262220, U.S. Pat. No. 7,612,199, US 2009/0130201 (rifaximin forms α, β and γ), WO 2006/094662 (rifaximin forms δ and ε), WO 2009/108730 (form ζ, form γ-1(ζ), form η, form α-dry, form ι, form β-1, form β-2, form ε-dry and various amorphous forms of rifaximin having characteristic X-ray diffraction peaks). U.S. Pat. No. 7,709,634 and WO 2008/035109 describe further amorphous forms of rifaximin.

Some technical and/or pharmaceutical properties such as solubility, intrinsic dissolution, bioavailability are reported only for some of the crystalline forms of rifaximin described in the literature. In particular, such information are available for rifaximin polymorphic forms α, β, γ, δ, ε and amorphous form.

Crystalline forms of rifaximin containing organic solvents are known, for instance WO 2009/108730 describes the form β-1, with an ethanolate/trihydrate of rifaximin.

WO 2012/150561 describes a solvate of rifaximin with N,N-dimethylformamide (DMF).

WO 2012/156951 describes a crystal of rifaximin κ obtained in presence of 1,2 dimethyl ether (DME).

The presence of organic solvents in the crystalline forms of rifaximin should be carefully monitored in medicinal products. Certain organic compounds have proven to be toxic for both humans and animals, leading health authorities to set maximum acceptable limits for these substances in products administered to humans.

For example, ethanol and DMF are organic solvents and their use in pharmaceutical compounds is regulated by European Guideline for residual solvent (CPMP/ICH/283/95). These guidelines divide organic solvents into three classes: Class 1, solvents which must be avoided; Class 2, solvents having an administration upper limit; Class 3, solvents with a low toxic potential, but having a maximum permitted daily dose (permitted daily exposure, PDE).

DMF, comprised in rifaximin κ as described in WO 2012/150561, belongs to the Class 3 and has a PDE of 8.8 mg. Taking into account that rifaximin-based pharmaceuticals can in some instances be administered in doses up to 2400 mg/die (Lorenzetti R. et al., Clin. Invest 2013, 3(12), 1187-1193), it must contain an amount corresponding to a rifaximin-DMF molar ratio larger than about 23:1 in order to keep the DMF exposure below the limit of 8.8 mg/die.

Although WO 2012/150561 does not explicitly mention the molar ratio between rifaximin and DMF, the described crystal contains at least one DMF mole for each rifaximin mole; in this case, the weight ratio between the two components would be 11:1, and consequently for a daily rifaximin dosage of 2400 mg, the DMF amount would be much larger than the safety limit permitted for this compound.

A similar case is represented by the crystalline form β-1, described in WO 2009/108730, containing ethanol, which has a PDE of 50 mg/die. Since the molar ratio reported between rifaximin and ethanol in crystalline form β-1 is 1:1, when rifaximin is administered at 2400 mg/die, the administered ethanol amount is about 141 mg/die, namely larger that the permitted amount for Class 3. Therefore, this crystalline form is also potentially toxic.

DME, described in WO 2012/156951 for the preparation of rifaximin κ, is a gaseous compound at room temperature, usually used as propeller and fuel, and should be avoided in industrial processes. Moreover, exposure to DME can have toxic effects, and it is reported that the exposure of pregnant rats to environments containing 1000 ppm DME has showed toxic effects both on the foetus and on the mother and studies on the exposure of rats and dogs showed cardiac arrhythmia and sedative effects as reported in Dupon Technical Information for 1,2 dimethyl ether (Dymel®).

All these observations lead to the conclusion that DME is potentially a toxic compound and its use in pharmaceutical preparations must be avoided. DME is easily inflammable and explosive and its potential industrial use for the preparation of rifaximin polymorphs is problematic.

The polymorphic form and the morphology of a solid form of a pharmaceutical compound can affect its physico-chemical and biological properties. Therefore it is important and useful to search new forms of a known compound that can be effectively and safely administered for medical use at a lower dosage and/or possess a different absorption profile in humans and animals. It is also important to find pharmaceutical preparations obtainable by industrial process.

The present invention describes a new crystalline form of rifaximin called rifaximin τ, which comprises in its crystalline structure, the compound identified by IUPAC nomenclature as 2-(2-ethoxyethoxy)ethanol, also known as diethylene glycol monoethyl ether, (DEGME), commercially available as a product under the trade name Transcutol® or Carbitol®.

The new crystalline form is a solvated stoichiometric form of rifaximin with a rifaximin:DEGME molar ratio of 1:1.

DEGME is a compound commonly used in the pharmaceutical industry and approved as a pharmaceutical excipient for its safety, and therefore easily usable. Several studies have shown that, per oral route, the NOAEL (No Observed Adverse Effect Level) value for DEGME is higher than about 160 mg/kg of body mass (European Commission, Health & Consumer Protection Directorate—General; Scientific Committee on Consumer Products [SCCP], Opinion on Diethylene Glycol Monoethyl ether [DEGME], 19 Dec. 2006). It follows that, in the case of a patient having a body weight of 70 kg, the DEGME daily administrable amount with no observed adverse effect is about 11200 mg. As a safety precaution, it is generally recommended that a toxic substance be administered at a dosage at least ten times lower than NOAEL; therefore, in the case of DEGME, doses lower than 1110 mg/die are deemed within the safe range. Where the molar ratio of rifaximin τ to DEGME is 1:1, this amount would correspond to a rifaximin dose of 6500 mg/die, which is higher than the typical dosages required in the pathologies treated with rifaximin.

Rifaximin τ is a stable form, and the crystalline structure does not transform when it is exposed to a humid environment at varying levels of humidity.

Rifaximin τ is a crystalline form of rifaximin with increased solubility in comparison with other crystalline forms, which provides high rifaximin concentrations in aqueous solution, maintaining a low absorption and avoiding systemic exposure. Said rifaximin τ does not show a proportional correspondence between solubility in aqueous solution and in vivo bioavailability values. The present invention also describes the process for obtaining the crystalline form of rifaximin τ, the pharmaceutical compositions comprising said form and their use in the treatment and/or prevention of infections and inflammations.

SUMMARY OF THE INVENTION

According to a first aspect, the present invention relates to a new crystalline form of rifaximin, characterized in that it is a solvated form of rifaximin with diethylene glycol monoethyl ether (DEGME) and it is called rifaximin τ.

The form of rifaximin τ is characterized by a tetragonal cell belonging to the space group $P4_12_12$ and by unit cell parameters a=b=16.51 (1) Å; c=36,80 (1) Å; α=β=γ=90°; V=10027(1) Å$^3$.

The form of rifaximin τ shows a X-ray diffraction spectra with peaks at values of angles 2θ±0.1° of 5.9°; 9.0° and 12.9°; or 5.9°; 12.9° and 18.8°; or 5.9°; 15.4° and 23.4°; or 9.0°; 15.4° and 23.4° or 12.9°; 22.8° and 23.4°.

The form of rifaximin τ is also characterized by a X-ray diffraction spectra with peaks at values of angles 2θ±0.1° of 5.9°; 9.0°; 12.9°; 15.4°; 18.8°; 22.8° and 23.4°.

Rifaximin τ is characterized in that it is a solvated form wherein the solvent is diethylene glycol monoethyl ether (DEGME) in a stoichiometric ratio of 1:1 with rifaximin.

Rifaximin is stable over time and does not transform into other forms when subjected to drying to remove water and/or other residual solvents present in the solid or when it is exposed to humidity. Rifaximin τ does not alter its chemical structure when exposed to humidity levels between 10% and 90% over a duration of time ranging from about 1 hour to 10 days.

Rifaximin τ is characterized by intrinsic dissolution values higher than 0.12 mg/min/cm$^2$.

Rifaximin τ is characterized by concentration values in aqueous solution at neutral pH higher than 90 μg/ml after 30 min.

Another aspect of the invention is a process for producing rifaximin τ comprising the steps of:
  adding diethylene glycol monoethyl ether (DEGME) to rifaximin, in a molar ratio ranging from about 4:1 to about 500:1, at temperatures ranging from room temperature to 100° C. for a duration of time ranging from 5 minutes to 5 hours to provide a rifaximin solution;
  cooling the solution to a temperature ranging from room temperature to −20° C.;
  filtering the obtained precipitate;
  drying the obtained precipitate at a temperature ranging from room temperature to 40° C. under a pressure ranging from ambient pressure to under vacuum, for a duration of time ranging from 5 minutes to 1 day.

The solid precipitate can be washed by the use of apolar solvent $C_3$-$C_7$ linear or cyclic or aromatic alkyl.

The process for producing rifaximin τ comprises the addition of diethylene glycol monoethyl ether (DEGME) in a molar ratio with rifaximin ranging from about 10:1 to about 100:1, preferably from about 50:1 to 100:1.

The process for producing rifaximin τ can further comprises a step of lyophilisation to dry the solid, and the solution to be lyophilized can comprise soluble carbohydrate, preferably trealose.

Another aspect of the invention is a pharmaceutical composition comprising an effective amount of the rifaximin τ together with one or more pharmaceutically acceptable excipients.

The pharmaceutical composition comprising rifaximin τ in an amount ranging from 20 and 1200 mg can be in the form of tablets, capsules, creams, or granules for suspension. The pharmaceutical composition of the invention can provide controlled release.

The pharmaceutical composition comprising rifaximin τ is useful as a medicament for the treatment or prevention of intestinal infections caused by, for example, *Escherichia coli, Clostridium difficile*, of traveller's diarrhoea, infectious diarrhoea and other intestinal disorders, for example, Crohn's disease, irritable bowel syndrome (IBS), enteritis, enterocolitis, diverticulitis, syndrome of the overgrowth of bacteria in the small intestine (SIBO), colitis, pancreatic insufficiency, chronic pancreatitis and/or hepatic encephalopathy, functional gastrointestinal disorder, functional dyspepsia with diarrhoea and other infections, for example, vaginal infections. Rifaximin τ is useful also as antibacterial or prophylactic prior to and post colon surgery, for dysentery, paucities, peptic ulcer disease and bacterial dysbiosis.

Rifaximin τ can be used as an analytical standard in X-ray analysis for complex mixtures of rifaximin.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

DETAILED DESCRIPTION

Figure 1:
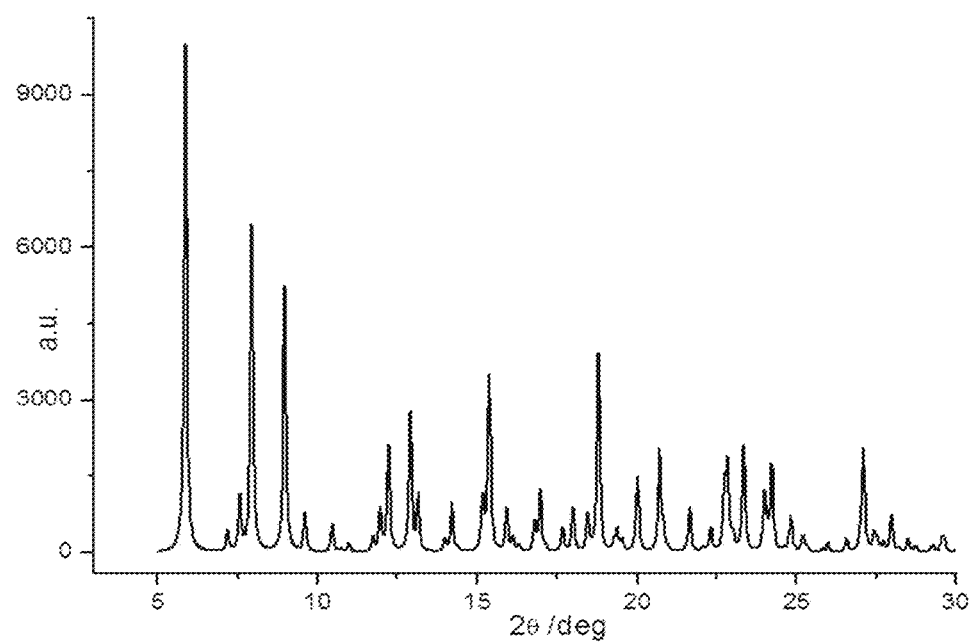
FIG. 1 illustrates an X-ray powder diffraction spectra (XRPD) obtained by single crystal cell parameters of rifaximin τ.

The present disclosure describes a rifaximin crystalline form and related compositions, methods and systems.

According to a first aspect, the invention relates to a new rifaximin crystalline form described herein as rifaximin τ, characterized in that it is a solvated form with diethylene glycol monoethyl ether, (DEGME).

Rifaximin τ is characterized by the related crystal system and related unit cell parameters, wherein crystal system is tetragonal, the space group is $P4_12_12$ and unit cell parameters are: a=b=16.51 (1) Å; c=36.80 (1) Å; α=β=γ=90°; V=10027(1) Å$^3$.

Rifaximin τ shows a X-ray diffraction spectra with peaks at values of angles 2θ±0.1 of 5.9°; 9.0° and 12.9° or 5.9°; 12.9° and 18.8° or 5.9°; 15.4° and 23.4° or 9.0°; 15.4° and 23.4° or 12.9°; 22.8° and 23.4°.

In some embodiments, rifaximin τ can be characterized by X-ray diffraction spectra with peaks at values of angles 2θ±0.1 of 5.9°; 9.0°; 12.9° and 18.8° or 5.9°; 12.9°; 15.4° and 18.8° or 9.0°; 12.9°; 15.5° and 18.8°.

In some embodiments, rifaximin τ can be characterized by X-ray diffraction spectra with peaks at values of angles 2θ±0.1 of 5.9°; 9.0°; 12.9°; 15.4°; 18.8°; 22.8° and 23.4°.

Rifaximin τ is solvated with a compound identified by IUPAC nomenclature as 2-(2-ethoxyethoxy)ethanol, also known as diethylene glycol monoethyl ether (DEGME), which can be identified through association with trademarks, such as Transcutol® or Carbitol®.

The term "solvate" as used herein, identifies a crystalline form containing a compound with a solvent, wherein the solvent is incorporated in the crystalline form as a component, and wherein the molar ratio between the two components forming the crystal form can be stoichiometric or not stoichiometric. The stoichiometric solvates can be considered molecular compounds and the solvent can be a part of the structure and can contribute to maintaining the crystal lattice of the crystal form or solvate.

Rifaximin τ can be described as a solvated stoichiometric form of rifaximin and DEGME, wherein rifaximin and DEGME are present in a stoichiometric molar ratio. In some embodiments, the stoichiometric molar ratio of rifaximin:DEGME is 1:1.

Rifaximin τ is stable and does not transform into other forms. In particular in some embodiments, rifaximin τ is stable over time. For example, rifaximin τ can maintain its crystal structure even when subjected to drying for removing water and/or other residual solvents present in the solid or when rifaximin τ is placed in humid environment. Accordingly, in several embodiments, physicochemical properties of rifaximin τ can be preserved in the storage of the active principle τ for the preparation of pharmaceutical compositions.

In some embodiments, rifaximin τ reaches concentrations in aqueous solution higher than those reached to other crystalline forms of rifaximin, and in some cases, dissolution values of rifaximin τ can be comparable to those of rifaximin amorphous forms. In addition, rifaximin τ can have values of intrinsic dissolution higher than those reported for hydrated crystal forms of rifaximin, and its value can be comparable with those of amorphous rifaximin Rifaximin τ can have intrinsic dissolution value higher than 0.10 mg/min/cm$^2$.

In some embodiments, rifaximin τ shows unexpected dissolution properties compared to the forms of rifaximin known in the art. For example, at pH 6.8, at time less than 1 hour, rifaximin τ provides higher concentration compared to rifaximin amorphous or rifaximin α. For example after about 30 minutes, rifaximin τ provides concentrations higher than 90 μg/ml. As the person skilled in the art will understand, such concentrations are about five times higher than those shown by amorphous rifaximin, for example, and about twenty times higher than those shown by rifaximin polymorph α or β. For example, in some embodiments, rifaximin τ reaches concentrations about 25 times higher than those obtained with rifaximin polymorph α.

In some embodiments, rifaximin τ shows pharmacokinetic values between those of rifaximin α and rifaximin amorphous.

In some embodiments, rifaximin τ shows $C_{max}$ values ranging from 0 to 35 ng/ml, $AUC_{0-8\,h}$ values ranging from 0 to 35 ng·h/ml and $AUC_{0-tlast}$ values ranging from 20 to 325 ng·h/ml.

In some embodiments, rifaximin τ reaches $C_{max}$ values at a longer time as compared to rifaximin α and amorphous rifaximin, at tmax values ranging from 3 to 7 hours.

In some embodiments, rifaximin τ reaches concentration in aqueous solutions higher than the other solid forms of rifaximin, but it does not show a proportional increase in bioavailability.

The increased dissolution rate of rifaximin τ, if compared to known forms of rifaximin, is not affected by the amount of DEGME present in the solution after the dissolution in aqueous solution. Compared to amorphous forms of rifaximin, crystalline form τ is more stable, and does not transform into other forms of rifaximin with different and uncontrolled physicochemical properties. In several embodiments, the rifaximin τ does not transform its crystallographic parameters and X-ray diffractogram when subjected to humidity levels ranging from about 10% to about 90% for a period ranging from about 1 hour to about 10 days, and does not transform into other, less soluble forms of rifaximin.

Rifaximin τ provides an increased concentration of rifaximin in aqueous solutions compared with other polymorph forms of rifaximin, without any proportional change of in vivo bioavailability. The ability of rifaximin τ to not transform into other crystal forms when exposed to environments with varying humidity, affects the pharmaceutical use of rifaximin τ. Rifaximin τ does not transform into other forms with different chemico-physical characteristics, and therefore provides a stable form which keeps the same properties of the starting compound, as solubility, bioavailability, local and systemic effectiveness and non-toxicity characteristics.

According to a second aspect, the invention relates to a process for obtaining rifaximin τ which allows the obtainment of this form in a reproducible way with a molar yield higher than 90%. The process for obtaining rifaximin τ comprises adding DEGME to rifaximin, in a DEGME:rifaximin molar ratios ranging from about 4:1 to about 500:1, at temperatures ranging from room temperature to 100° C. for a duration ranging from 5 minutes to 5 hours, until complete dissolution of rifaximin starting material.

In some embodiments, the DEGME can be added to the rifaximin in a DEGME:rifaximin molar ratio ranging from about 50:1 to about 100:1.

In some embodiments, the adding of DEGME to solid rifaximin can be performed in a molar ratio of DEGME: rifaximin ranging from about 4:1 to about 500:1, and in particular the DEGME:rifaximin molar ratio can range from about 10:1 to about 100:1.

In some embodiments, the adding step can be performed by dissolving rifaximin in DEGME and the method can comprise dissolving rifaximin in DEGME, thereby obtaining a solution; and cooling the solution to a temperature ranging from room temperature to −20° C., thereby filtering the precipitated solid from the solution and drying the solid.

In some embodiments, the adding of DEGME to rifaximin results in a rifaximin suspension in DEGME that can be stirred at a temperature ranging from room temperature to 100° C. for a duration of time ranging from 5 minutes to 5 hours until complete dissolution of rifaximin. The solution can be kept at room temperature or at a temperature ranging from room temperature to 60° C.

In some embodiments, an apolar solvent such as n-pentane, n-hexane, or n-heptane can be added to rifaximin-DEGME solution. Rifaximin τ can precipitate in a time ranging from 1 hour to 20 hours as an intensely coloured solid. The solid can then be filtered and dried. In those embodiments, the solid can be washed with apolar organic solvents, such as n-pentane, n-hexane, or n-heptane.

In some embodiments, excess of DEGME and/or other solvent(s) can be removed by filtration, by absorption on inert absorbent material, by evaporation, by evaporation under vacuum, or by means of a combination of these methods. The drying step can take place, for example, at a temperature ranging from room temperature to 70° C., and under a pressure ranging from ambient pressure to a reduced pressure of about 0.001 Torr. The drying time can range from about 10 minutes to about 1 day, and optionally in the presence of dehydrating agents. In some embodiments, the drying can be performed under vacuum and in some of those embodiments, a condenser can also be used in connection with the vacuum system at temperatures ranging from room temperature to 40° C.

In some embodiments, the process for obtaining a rifaximin crystalline form comprises the steps of:
dissolving rifaximin in diethylene glycol monoethyl ether (DEGME), in a DEGME:rifaximin molar ratio ranging from about 4:1 to about 500:1, at temperatures ranging from room temperature to 100° C., for a duration of time ranging from 5 minutes to 5 hours to obtain a rifaximin solution;
cooling the solution to a temperature ranging from room temperature to −20° C. and over a duration of time ranging from 1 hour to 20 hours;
filtering the solution to obtain a rifaximin precipitate;
drying the precipitate at a temperature ranging from room temperature to 40° C. under a pressure ranging from ambient pressure to 0.001 Torr, for a duration of time ranging from 10 minutes to 1 day, and optionally in the presence of dehydrating agents.

The solid precipitate can be washed with apolar organic solvent, e.g. $C_3$-$C_7$ linear or cyclic or aromatic alkyl.

In some embodiments, the process described herein can provide a rifaximin solvate in crystalline form, with a process yield higher than 90%. In some embodiments, the process for obtaining rifaximin τ described herein allows for obtaining this crystalline form in a reproducible way with a molar yield between 30% and 99%.

Rifaximin τ obtained with a process described herein can have a purity of higher than about 95%, and can be obtained with an experimental yield from about 40% to about 90%.

The process described herein generates a rifaximin crystalline form characterized by a X-ray diffraction spectra with peaks at values of angles 2θ±0.1 of 5.9°; 9.0° and 12.9° or 5.9°; 12.9° and 18.8° or 5.9°; 15.4° and 23.4° or 9.0°; 15.4° and 23.4° or 12.9°; 22.8° and 23.4° (see FIG. 1).

Accordingly, in some embodiments, the present disclosure relates to the use of DEGME for solubilising rifaximin in a production process for rifaximin τ and rifaximin related compositions.

In particular, in some embodiments, DEGME can be used in a molar ratio ranging from 4 to 100 times relative to rifaximin. In some embodiments, DEGME can be used to solubilise the starting rifaximin in a molar ratio ranging from 4 to 500 times relative to rifaximin, in particular ranging from 10 to 100 times relative to rifaximin. In the use of DEGME described herein, excess DEGME on the crystalline surface is removed by washing with an apolar organic solvent, preferably $C_3$-$C_7$ linear or cyclic alkyl and/or by drying. DEGME residual can be comprised in finished pharmaceutical compositions, without any toxic effect. In some embodiments, the rifaximin used for the preparation of the new crystalline form can be in a polymorph, amorphous or raw form, or mixtures thereof.

In some embodiments, DEGME can be used to obtain rifaximin τ in a rifaximin crystalline stoichiometric solvate wherein DEGME and rifaximin components are in a molar ratio of 1:1.

A third aspect of the invention relates to pharmaceutical compositions comprising a therapeutically effective amount of rifaximin τ. In particular, in some embodiments, a pharmaceutical composition is described that comprises a therapeutically effective amount of rifaximin τ or its derivatives together with one or more pharmaceutically acceptable excipients for the treatment and/or the prevention of inflammations and infections, such as, for instance, intestinal, vaginal or lung infections.

The term "derivatives" as used herein with reference to rifaximin τ indicates salts, enantiomers, co-crystal and additional derivatives identifiable by a skilled person.

The term "pharmaceutically acceptable excipients" indicates any of various media acting usually as solvents, carriers, binders or diluents for the rifaximin comprised in a composition as an active ingredient. Exemplary pharmaceutically acceptable excipients in the sense of the present disclosure include lubricants, glidants, diluents, buffering agents, opacifiers, plasticizers and colouring agents, agents capable of providing a controlled release and agents capable of providing bio-adhesive properties.

In some embodiments, compositions comprising rifaximin τ can provide a higher rifaximin concentration in aqueous solutions compared to other crystalline forms of rifaximin and provides a low amount of rifaximin in vivo.

In some embodiment rifaximin τ provides increased local concentration with low systemic absorption.

In some embodiments, when rifaximin τ is in solid compositions (e.g. in tablets) with pharmaceutically excipients, the amount of soluble rifaximin released is in a higher percentage than that released by compositions comprising hydrated crystalline rifaximin or amorphous rifaximin.

In several embodiments, pharmaceutical compositions comprising rifaximin τ can release a higher amount of rifaximin as soluble rifaximin and the release of soluble rifaximin is considered rapid. Reference is made to Example 15 which demonstrates that tablets comprising rifaximin τ release nearly five times the amount of rifaximin as compared to the amount released by a tablet comprising another form of crystalline rifaximin. In some embodiments, tablets comprising rifaximin τ release, after 45 minutes, an amount of rifaximin that is 40% higher than the amount of rifaximin released by a tablet containing amorphous rifaximin.

An increased concentration of rifaximin is useful for topical infection or inflammations.

A form of rifaximin characterized by providing intermediate and different dissolution profile in comparison with known forms of rifaximin, is useful to provide balanced and modulated local and in vivo absorption.

In some embodiments, the release can be modified according to the conditions treated by these compositions.

In some embodiments, rifaximin τ can also be associated with other crystalline forms of rifaximin, such as, for example, the forms α, β, γ, δ, ε, β-1, ζ, η, ι, κ, θ, μ, ο, π, λ, ξ, mesylate form, amorphous forms or solid dispersion, or their mixtures. The use of mixtures of these forms with rifaximin τ in defined ratios can lead to a different bioavailability of rifaximin and therefore to various uses in different kinds of infections and/or different kinds of intestinal disorders.

In some embodiments, the pharmaceutical composition described herein can comprise rifaximin τ in an amount ranging from about 20 mg to about 3300 mg.

In some embodiments, pharmaceutical compositions can be in the form of a powder, paste, granulates, tablets, capsules, pessaries, cream, ointment, suppository, suspension or solution. In some embodiments, pharmaceutical composition can be formulated for use in humans. In some embodiments, the pharmaceutical composition can be formulated for use in animals.

Pharmaceutical compositions described herein can be prepared based on rifaximin τ by mixing rifaximin τ with one or more pharmaceutical excipients to obtain a pharmaceutical composition The mixing can be performed according to methods and techniques identifiable by a skilled person upon reading of the present disclosure. In particular, the mixing can be performed to obtain a pharmaceutical composition comprising rifaximin τ and at least one excipient in a set pharmaceutical form.

The term "pharmaceutical form" in the sense of the present disclosure relates to a pharmaceutical product involving a mixture of active drug components and nondrug components (excipients), along with other non-reusable material that cannot be considered either ingredient or packaging (such as a capsule shell, for example). Depending on the method/route of administration, pharmaceutical forms come in several types. These include liquid, solid, and semisolid dosage forms.

In some embodiments, the pharmaceutical composition described herein can be in solid or liquid form, in a suspension, in a gel, as a cream, as a foam, or as a spray. For example, the pharmaceutical compositions described herein, can be in the form of pills, tablets, capsules, soft capsules, granules, enemas, syrups, gels, emulsions, suppositories, and in additional forms identifiable by a skilled person also in view of the condition to be treated and the route of administration. For example in some embodiments, rifaximin τ can be used for preparations for rectal or vaginal use, in the form of douches, tablets, pessaries, or the like.

In some embodiments, the pharmaceutical compositions described herein can be a controlled release compositions, such as an immediate release or slow release or delayed release or a gastroresistant composition for release of the active principle in the intestine. The amount of the rifaximin τ in the pharmaceutical compositions can provide for a form of dosage which varies according to the administration method and corresponding to the amount necessary to obtain the desired therapeutic or preventive effect. For example, the amount of rifaximin τ can be from 0.1% to 99% compared to the weight of the final composition. According to some aspects of the present disclosure, the active principle is an amount by weight ranging from 1% to 80%, preferably from 10% to 70% of the weight of the final composition.

In some embodiments, the compositions described herein can be in the form of tablets comprising rifaximin τ, wherein said form has a weight percentage ranging from 20% to 70% in respect to the weight of the tablet.

In some embodiments, the one or more excipients can comprise lubricants, glidants, disintegrants, diluents, buffering agents, pacifiers, plasticizers and colouring agents, agents capable of providing a controlled release and agents capable of providing bio-adhesive properties.

In these compositions, rifaximin τ can be directly mixed with excipients known in the pharmaceutical art for obtaining a solid form, such as, for example, a tablet which can also be coated with suitable coatings to provide for controlled release. The release can also be immediate, delayed or gastroresistant according to the aim of the administration.

In some embodiments, rifaximin τ can be mixed with excipients to form granules which can be used as such or mixed with extragranular excipients to form solid compositions such as, for example, tablets. In some embodiments, granular excipients can be chosen among known excipients in the pharmaceutical art which are suitable to provide a controlled release. Granules comprising rifaximin τ can have 20% to 90% by weight of the finished composition.

In some embodiments, rifaximin τ can be in the granules in an amount from 10% to 80% with disintegrant(s) in an amount from 5% to 20%, diluents(s) in an amount from 5% to 70%, glydant(s) in an amount 0.1 to 5% in respect to the weight of granule.

In some embodiments, tablets comprising granules of rifaximin τ can be successively coated with suitable coatings to stabilize the pharmaceutical form or to guarantee a controlled release of rifaximin, for example, enteric coatings.

In some embodiments, the granules comprising rifaximin τ can be coated to form controlled release granules, such as, for example, release at pH higher than 4.5. The controlled release granules can be used in solid forms, such as, for example, tablets or sachets for oral suspensions. In sachet compositions for aqueous solutions, the amount of these granules can be 5% and 50% by weight of the finished composition.

The pharmaceutical compositions according to the present disclosure can be prepared according to the methods known in the pharmaceutical art with a carrier or one or more excipients or in association with other active principles. The dosage of the rifaximin crystal is incorporated in the pharmaceutical composition of the present disclosure and can depend on the disease and on the treatment schedule.

In some embodiments, the compositions of rifaximin τ can be in form of tablets wherein rifaximin can be, for example, in the form of powder or in the form of granules mixed together with pharmaceutically acceptable excipients.

In embodiments wherein rifaximin τ is in the form of granules, the granules can comprise granular excipients such as, for example, disintegrants, lubricants, diluents and glidants. The rifaximin τ granules can be successively mixed with extragranular excipients comprising lubricants, glidants, diluents and disintegrants. In some embodiments of the pharmaceutical compositions described herein, granular excipients comprise a substance selected from starch glycolate, glyceryl stearate, talc, microcrystalline cellulose and extragranular excipients selected from glyceryl palmitostearate, talc, microcrystalline cellulose and silica.

In some embodiments, tablets can comprise rifaximin granules in an amount from 20% to 90% in respect to the weight of tablets.

In some embodiments, extragranular excipients can comprise diluents(s) in an amount from 5% to 10%, disintegrant(s) in an amount from 1% to 5% and glydant(s) in an amount from 0.1% to 1% in respect to the weight of the tablets.

In some embodiments, compositions such as tablets obtained by mixing rifaximin τ in powder or granule form with suitable excipients can then be coated with suitable coatings to provide for a controlled release of rifaximin.

In some embodiments, tablets comprising rifaximin τ can be prepared by directly mixing rifaximin τ with excipients, and the core obtained by compression or compacting, suitably coated to provide for the desired release.

In some embodiments, the tablets can be coated with gastroresistant coatings suitable to release rifaximin at pH values higher than 4.5. These coatings can contain commercially available gastroresistant polymers.

In some embodiments, the compositions comprising rifaximin τ can be in form of granules of solvated rifaximin together with excipients such as sweeteners, flavouring agents, diluents, plasticizers, and/or anti-foaming agents for preparations in sachets for generating aqueous suspensions.

In embodiments described herein, the disintegrants can be selected, for example, among cellulose derivatives such as sodium carboxymethyl cellulose also called carmellose, crosslinked carboxymethyl cellulose, also called croscarmellose, hydroxypropyl methylcellulose, hydroxypropyl ethylcellulose, hydroxypropyl cellulose phthalate, polyvinyl acetate phthalate, povidone, copovidone, or sodium starch glycolate.

In embodiments described herein, the lubricants can be selected, for example, among magnesium or calcium stearate, sodium stearyl fumarate, hydrogenated vegetable oils, mineral oils, polyethylene glycols, sodium lauryl sulphate, glycerides, sodium benzoate, or mixtures thereof.

In embodiments described herein, the diluents can be selected, for example, among cellulose, microcrystalline cellulose, calcium phosphate, starch, kaolin, anhydrous or hydrated calcium sulphate, calcium carbonate, lactose, sucrose, mannitol, starches, natural gums, malt, or gelatine.

In embodiments described herein, the glidants can be selected, for example, among talc, microcrystalline cellulose, or magnesium carbonate.

In embodiments described herein, the plasticizers can be selected, for example, among adipates, azelates, benzoates, citrates, phthalates, sebacates, stearates and glycols, such as acetylated monoglycerides, butyl glycol, dibutyl tartrate, diethyl phthalate, dimethyl phthalate, ethyl phthalate, ethyl glycol, glycerol, ethylene glycol, propylene glycol, triacetin citrate, dibutyl phthalate, polyethylene glycols, castor oil, polyhydric alcohols, acetate esters, glycerol triacetate, dibenzyl phthalate, dihexyl phthalate, butyl octil-phthalate, caprilates or caprates. The amount of plasticizers used in the compositions can vary, for example, between about 5% and about 50%.

In some embodiments, the compositions described herein can comprise a protective layer which can be used over the enteric layer or over other layers including a semi permeable polymer which can cover the enteric layer to reduce the penetration of water or to increase the time range for releasing rifaximin. Apparatuses like the fluidized bed, in which the polymers are dissolved in water or in organic solvents, can be used for coating with these polymers.

In embodiments described herein, the compositions can also comprise anti-foaming agents, buffering agents, such as magnesium hydroxide, aluminium hydroxide, alginic acid, pyrogen-free water, isotonic saline solutions, ethyl alcohol, phosphate buffer solutions and other non-toxic substances compatible for pharmaceutical use.

In embodiments described herein, other agents can be added to the solution to increase its processability, such as talc, colloidal silica, polyvinyl alcohol, glycerol monostearate, magnesium tri-silicate, magnesium stearate, and mixtures thereof.

In embodiments described herein, the amount of polymers to be used to give the composition the desired release properties can be adjusted to achieve the desired purpose.

In embodiments described herein, the compositions in tablets or granules in sachets can contain sweeteners such as sucrose, mannitol, sorbitol, saccharin, acesulfame or neohesperidine or their mixtures. In embodiments of the compositions described herein, colouring and flavouring agents can be comprised in the compositions.

In embodiments of the compositions described herein, preservatives and antioxidants such as, ascorbic acid, cysteine, sodium bisulfite, sodium metasulfite, sodium metabisulfite, or sodium sulphite, and chelating agents such as citric acid, ethylenediaminetetraacetic acid (EDTA), sorbitol, tartaric acid, or phosphoric acid, can be included.

In some embodiments, other ingredients of the compositions described herein can comprise polysaccharides, such as starch, chitosan, chondroitin sulphate, dextran, guar gum, xyloglucan, xanthans, inulin, pectin, firming agents such as adipates, azelates, benzoates, citrates, phthalates, stearates and glycols, cellulose acetate, cellulose acetate butyrate, cellulose acetate propionate, ethyl cellulose, fatty acids and their esters, waxes and zeins.

In embodiments described herein, optionally, hydrophilic polymers such as hydroxyethyl cellulose and hydroxypropyl cellulose can be added.

In embodiments described herein, agents providing mucoadhesivity to the composition can optionally be added. In some embodiments, tablets and granules described herein can be coated with filmogen coatings comprising, for example, microcrystalline cellulose, hydroxymethyl or hydroxypropylmethyl cellulose, opacifiers, such as titanium dioxide, plasticizers such as propylene glycol and optionally colouring, flavouring and/or buffering agents.

In some embodiments, tablets and granules described herein can be coated with suitable coatings to provide a controlled release, for example, a quick release or a late release or an intestinal release.

In some embodiments, the compositions can comprise gastroresistant agents wherein the rifaximin τ granules or the tablets are coated with suitable agents to release rifaximin at pH values greater than 4.5, for example pH values comprised between about 4.9 and 7.7. Exemplary agents comprise acrylic polymers, methacrylic acid copolymer with an acrylic or methacrylic ester (e.g., copolymer of methacrylic acid (1:1) and copolymer of methacrylic acid and methyl methacrylate (1:2), polyvinyl acetate phthalate, hydroxypropyl cellulose acetate phthalate and cellulose acetate phthalate), cellulose acetate phthalate, hydroxypropyl methylcellulose phthalate, polyvinyl acetate phthalate. These products are commercially available under the trademarks EUDRAGIT®, EUDRAGIT® RL, EUDRAGIT® 40, AQUATERIC®, AQUACOAT®.

In some embodiments of the pharmaceutical composition described herein, enteric or gastroresistant polymers, which are soluble at high pH values, can be used for specific colon release. In some of those embodiments, enteric or gastroresistant polymers can be used for gastroresistant formulations such as those described, although not limited to those described. The gastroresistant polymers used can also be modified by adding other coating products which are not pH sensitive, such as products comprising acrylic esters, esters of methacrylic acid with a small portion of trimethylammonium ethyl methacrylate chloride, polysaccharides such as amylose, chitosan, chondroitin sulphate, dextran, guar gum, inulin and pectin.

In some embodiments, gastroresistant polymers in pharmaceutical compositions described herein can be in concentrations ranging from about 5% to about 75% by weight of the final composition. According to a particular aspect of the present disclosure, the concentration can be range from about 20% to about 60%.

In some embodiments, the gastroresistant microgranules can have bioadhesive properties, which means that they can adhere to the mucosa. Exemplary polymers and oligomers, or mixtures thereof that can be included in microgranules described herein are pectins, zeins, casein, gelatine, albumin, collagen, chitosan, oligosaccharides and polysaccharides such as cellulose, dextran, polysaccharides from tamarind seeds, xanthan gum, gum arabic, hyaluronic acid, alginic acid, and/or sodium alginate.

In embodiments, where the bioadhesive polymer is a synthetic polymer, the polymer can be selected from polyamides, polycarbonates, polyalkylenes, polyalkylene glycols, polyalkylene oxides, polyalkylene terephthalates, polyvinyl alcohols, polyvinyl ethers, polyvinyl esters, polyvinyl pyrrolidone, polysiloxanes, polyurethanes, polystyrenes, polymers of acrylic acid and methacrylic esters, copolymer of methacrylic acid-ethyl acrylate, polylactides, poly acids barbiturates, polyanhydrides, polyorthoesters, and mixtures thereof.

Other polymers that can be comprised in compositions described herein include, for example, methylcellulose, ethyl cellulose, hydroxypropyl cellulose, hydroxybutylmethyl cellulose, cellulose acetate, cellulose propionate, cellulose acetate butyrate, cellulose acetate phthalate, carboxymethyl cellulose, cellulose triacetate, cellulose sulphate sodium salt, polymethyl methacrylate, poly isopropyl methacrylate, poly isobutyl acrylate, polyoctadecyl acrylate, polypropylene, polyethylene glycol, polyethylene oxide, polyethylene terephthalate, polyvinyl acetate, polyvinyl chloride, polystyrene, polyvinyl pyrrolidone, polyvinyl phenol and/or mixtures thereof.

Another group of polymers useful for bioadhesivity in the compositions described herein includes polymers having a branching with at least one linked hydrophobic group, in which the hydrophobic groups are generally non-polar groups. Examples of these hydrophobic groups comprise alkyls, alkenyls and alkynyl groups. The hydrophobic groups can be chosen to increase the bioadhesivity of the polymers. Other polymers are characterized by hydrophobic branchings with at least a hydrophilic group, such as carboxylic acids, sulfonic acids and phosphonic acids, neutral and positively charged amines, amides and imines, wherein the hydrophilic groups are such to increase the bioadhesivity of the polymer.

In some embodiments, the compositions in tablets can be prepared with the methods known in the art, for example with rifaximin granules. The tablets can contain a rifaximin core or a rifaximin layer in multilayer tablets in which the other layers can contain other useful active principles for a combined administration, or suitable agents to control the rifaximin release.

In some embodiments, compositions containing the solvated form of rifaximin can be useful for oral administrations, and can be in form of tablets, pills, granules for suspension in aqueous or hydroalcoholic solutions, or elixirs, each containing an effective amount of the new rifaximin form.

In some embodiments, the compositions comprising the rifaximin form of the present disclosure can also be in the form of a cream for topical use, rectal use or suppositories prepared by any method known in the art. In those embodiments, the amount of rifaximin τ can be combined with a carrier to produce a therapeutic effect.

In some embodiments, the preparations are in the form of a cream that can contain the excipients known in the art, such, for example, as white petrolatum, white wax, lanolin and its derivatives, stearyl alcohol, propylene glycol, sodium lauryl sulphate, fatty acid esters, stearate, cellulose, colloidal aluminium, magnesium silicate, and sodium alginate.

Another aspect of the invention includes pharmaceutical compositions comprising rifaximin τ for medical use. The pharmaceutical compositions of rifaximin τ are useful in the treatment or prevention of intestinal infections, for example, *Escherichia coli, Clostridium difficile*, and of traveller's diarrhoea, infectious diarrhoea and other intestinal disorders, for example, Crohn's disease, irritable bowel syndrome (IBS), enteritis, enterocolitis, diverticulitis, syndrome of the overgrowth of bacteria in the small intestine (SIBO), colitis, pancreatic insufficiency, chronic pancreatitis, hepatic encephalopathy, functional gastrointestinal disorders, functional dyspepsia with diarrhoea and other infections, for example, vaginal infections. The pharmaceutical compositions of rifaximin τ are useful as an antibacterial or prophylactic treatment prior to and post colon surgery, or for dysentery, paucities, and/or peptic ulcer disease.

The pharmaceutical compositions comprising rifaximin τ can provide increased local concentrations of rifaximin and be efficacious at lower amounts of rifaximin or provide efficacy for severe infection or inflammation.

In some embodiments, the pharmaceutical compositions described herein can be administered to provide rifaximin τ in a dosage range from 20 to 3300 mg per day.

In some embodiments, the dosage of the administered active principle rifaximin τ can range from about 20 to 2400 mg/day, preferably comprised between 50 and 1200 mg/day. In some of those embodiments, the compositions can, for example, be administered one, twice or three times a day.

In some embodiments, rifaximin τ can be administered once a day, twice a day, three times a day, four times a day or even more often, if necessary, at doses ranging from 20 mg to 3300 mg/die. Exemplary doses comprise from 100, 200, 400, 550, 600, 800 mg/die up to 1100 mg/die. In some embodiments, 100, 200, 400, 550, 600, 800 mg/die or more of rifaximin τ can be administered once a day, twice a day, three times a day, four times a day, or even more often if necessary.

The pharmaceutical compositions comprising rifaximin τ can provide increased local concentrations of rifaximin also providing efficacious at lower amount of rifaximin or efficacious for severe infection or inflammation.

The rifaximin τ and related compositions can be used for treatment and/or prevention of a condition in an individual.

The term "treatment" as used herein indicates any activity that is part of a medical care for, or deals with, a condition, medically or surgically. The terms "treating" and "treatment" refer to reduction in severity and/or frequency of symptoms, elimination of symptoms and/or underlying cause, prevention of the occurrence of symptoms and/or their underlying cause, and improvement or remediation of damage. Thus, for example, "treating" a patient involves prevention of a symptom or adverse physiological event in a susceptible individual, as well as modulation and/or amelioration of the status of a clinically symptomatic individual by inhibiting or causing regression of a disorder or disease.

The term "prevention" as used herein with reference to a condition indicates any activity which reduces the burden of mortality or morbidity from the condition in an individual. This takes place at primary, secondary and tertiary prevention levels, wherein: a) primary prevention avoids the development of a disease; b) secondary prevention activities are aimed at early disease treatment, thereby increasing opportunities for interventions to prevent progression of the disease and emergence of symptoms; and c) tertiary prevention reduces the negative impact of an already established disease by restoring function and reducing disease-related complications.

The term "condition" indicates a physical status of the body of an individual (as a whole or as one or more of its parts e.g., body systems), that does not conform to a standard physical status associated with a state of complete physical, mental and social well-being for the individual. Conditions described herein include disorders and diseases wherein the term "disorder" indicates a condition of the living individual but that is associated to a functional abnormality of the body or of any of its parts, and the term "disease" indicates a condition of the living individual that impairs normal functioning of the body or of any of its parts and is typically manifested by distinguishing signs and symptoms in an individual.

The term "individual" or "subject" or "patient" as used herein in the context of treatment includes a single animal and in particular higher animals and in particular vertebrates such as mammals and in particular human beings. In general "individual" according to the present disclosure indicates an animal that has a gastrointestinal (herein also GI) system and that is susceptible to gastric and intestinal ulcerations, as well as a respiratory system and a reproductive system.

In particular, in embodiments described herein, rifaximin τ and related compositions are useful for the treatment of various conditions in inflammations and infections, such as, for example, systemic, intestinal, vaginal, cutaneous and pulmonary ones. In particular, a higher solubility of rifaximin τ, compared to other forms of rifaximin known in the art, can be useful for the treatment of various conditions in inflammations and infections, such as, for example, intestinal, vaginal and pulmonary ones, wherein a higher local concentration is efficacious. Rifaximin τ is characterized by a high topical effect with a low in-vivo absorption and this is a very important for the low toxicity and interaction with other active ingredients.

As with other pharmaceuticals, it will be understood that the total daily usage of one or more pharmaceutical compositions of the present disclosure will be decided by a patient's attending physician within the scope of sound medical judgment. The specific therapeutically effective or prophylactically effective dose level for any particular patient will depend upon a variety of factors including the disorder being treated and the severity of the disorder; activity of the specific compound employed; the specific composition employed; the age, body weight, general health, sex and diet of the patient; the time administration, route of administration, and rate of excretion of the specific compound employed; the duration of the treatment; drugs used in combination or coincidental with the specific compound employed; and other factors known to those of ordinary skill in the medical arts.

In another embodiment, the present invention relates to the use of the single crystal of rifaximin τ, as internal standard, in X-ray analysis.

The term "mixture" as used herein indicates two or more substances which have been combined such that each substance retains its own chemical identity in particular a mixture can be a material system made up of two or more different substances which are mixed but are not combined chemically and can take the form of in the form of solutions, suspensions, and colloids. Mixtures can be either homogeneous or heterogeneous. A homogeneous mixture is a type of mixture in which the composition is uniform and every part of the solution has the same properties. A heterogeneous mixture is a type of mixture in which the components can be seen, as there are two or more phases present.

In some embodiments, a single crystal of rifaximin τ can be used to detect rifaximin τ in a mixture of rifaximin, possibly further comprising other crystal forms and amorphous forms of rifaximin.

In some embodiments, the method described herein can comprise obtaining an X-ray powder diffraction pattern of the mixture, and comparing the X-ray powder diffraction pattern of the complex mixture with an X-ray powder diffraction pattern of the single crystal of rifaximin τ.

In some embodiments, obtaining an X-ray diffraction pattern can be performed by placing the mixture in a X-ray diffractometer and providing an intense beam of X-rays, on the mixture usually of a single wavelength (monochromatic X-rays), producing a regular pattern of reflections, thus providing an X-ray diffraction pattern of the mixture.

In some embodiments, the X-ray diffraction pattern of the mixture can be compared with the X-ray diffraction patter for rifaximin τ to identify common peaks characterizing rifaximin τ over other compounds including other forms of rifaximin. In particular, in some embodiments identifying rifaximin τ in the mixture is performed by detecting peaks from the X-ray powder diffraction pattern of the single crystal of rifaximin τ in the X-ray powder diffraction pattern of the mixture.

In some embodiments, the present disclosure relates to the use of a single crystal of rifaximin τ as a standard, to determine the presence of this form in mixtures of other crystal forms and amorphous forms of rifaximin. In some embodiments, the standard can be provided by an X-ray diffraction pattern of the single crystal rifaximin τ In some embodiments, the X-ray diffraction pattern of the single crystal rifaximin τ can be calculated based on the structural details. In some embodiments, the X-ray diffraction pattern of the single crystal rifaximin τ can be experimentally provided.

In some embodiments, presence of rifaximin can be identified by comparing an X-ray powder diffraction pattern of the mixture with the standard to detect rifaximin τ in the mixture.

In some embodiments, given the structural details, crystallographic system, space group, cell parameters and fractional coordinates of the atoms in the structure, it is possible to calculate the X-ray powder diffraction pattern and to compare this with any experimental one. The coincidence of relevant peaks in the two patterns allows identification of rifaximin τ in a mixture or in the presence of amorphous solid. The calculated pattern can be used to detect the presence of rifaximin τ in a solid mixture by comparison with an experimental pattern and also to normalize the peaks values.

Further advantages and characteristics of the present disclosure will become more apparent hereinafter from the following detailed disclosure by way of illustration only with reference to examples, which are reported for purely illustrative purposes and in no way limiting the scope of the present disclosure.

EXAMPLES

The compositions, methods and systems described herein are further illustrated in the following examples, which are provided by way of illustration and are not intended to be limiting.

In particular, the following examples illustrate exemplary compositions and related methods and systems of the present disclosure. A person skilled in the art will appreciate the applicability and the necessary modifications to adapt the features described in detail in the present section, to additional compositions, methods and systems according to embodiments of the present disclosure.

Example 1

Method of Preparation Rifaximin τ (I)

An amount corresponding to 2300 mg diethylene glycol monoethyl ether (also named 2-(2-ethoxyethoxy)ethanol) and herein (DEGME), was added to 20 mg of rifaximin polymorph α and the suspension stirred at room temperature until complete dissolution. The solution was allowed to evaporate at room temperature and after four days, coloured crystals were formed, isolated and analysed.

Example 2

Determination of the Crystalline Structure of Rifaximin

The structural determination of rifaximin τ obtained according to Example 1 was carried out by means of an Oxford Diffraction Xcalibur, provided with a CCD area detector using the MoKα (λ=0.71073 Å) radiation and a graphite monochromator; data were collected at room temperature. The structure was solved by using direct methods by means of the program SIR2008 (M. C. Burla, R. Caliandro, M. Camalli, B. Carrozzini, G. L. Cascarano, L. De Caro, C. Giacovazzo, G. Polidori, D. Siliqi, R. Spagna (2007); *Il Milione*: a suite of computer programs for crystal structure solution of proteins *J. Appl. Cryst.* (2007), 40, 609-613)) and refined by means of the program SHELX97 (Sheldrick, G. M. *SHELX97, Program for Crystal Structure Determination*; University of Göttingen: Göttingen, Germany, 1997, implemented by means of the package WingX (L. J. Farrugia, *J. Appl. Cryst.* (2012), 45, 849-854. Table 1 reports structural and measurements details of the crystal of the present disclosure.

TABLE 1

| Chemical formula | $C_{43}H_{51}N_3O_{14} \cdot C_6H_{14}O_3$ |
| --- | --- |
| Molecules of H$_2$O per rifaximin molecule | 0 |
| Temperature/K | 295 |
| Morphology | Prism |
| Crystal system | Tetragonal |
| Space group | P4$_1$2$_1$2 |
| a/Å | 16.5063 (5) |
| b/Å | 16.5063 (5) |

TABLE 1-continued

| c/Å | 38.801 (2) |
| --- | --- |
| β/deg | 92.180 (1) |
| V/Å$^3$ | 10026.72 (1) |
| Z | 8 |

FIG. 1 reports the X-ray diffractogram of rifaximin τ obtained on the basis of single crystal data.

Example 3

Method of Preparation of Rifaximin τ (II)

Amounts of DEGME in a molar ratio of 64:1 relative to rifaximin were added to solid rifaximin. The suspension was kept under stirring at 60° C. until a clear solution was obtained. The solution was left to cool to room temperature and kept one night under stirring. The solid precipitate was filtered and dried from the excess of solvents by means of absorbing paper. The crystal powder was sieved by means of a 100 μm sieve, thus obtaining a crystal product which, once analyzed by HPLC, gave a rifaximin titre of 69.9%; once analyzed by GC, a DEGME titre of 28.53% was obtained; once analyzed by the Karl Fisher method, a water content of 1.58% was measured.

Figure 2:
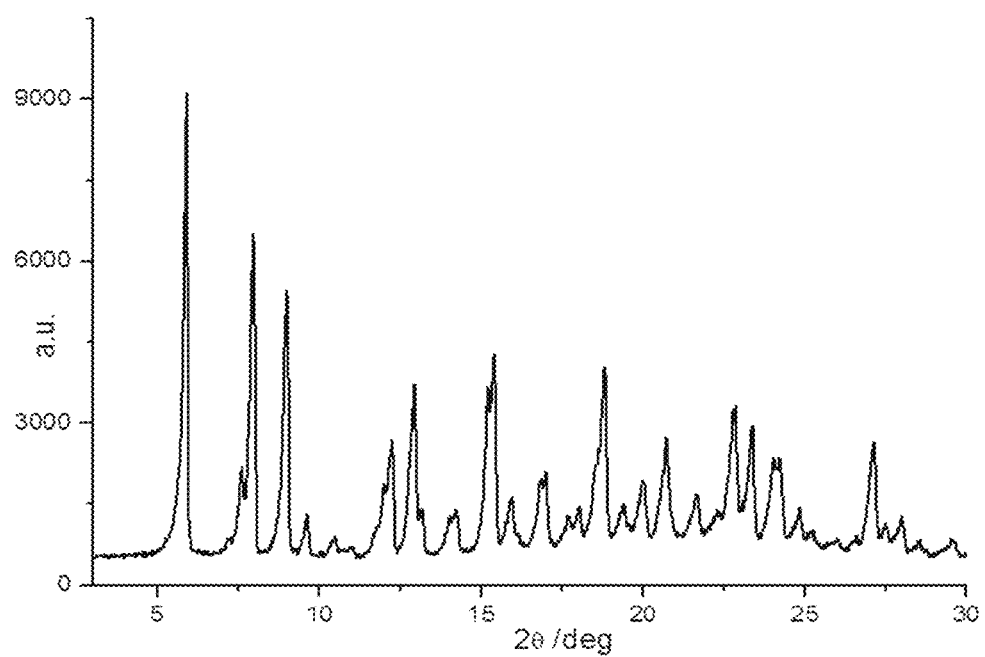
FIG. 2 illustrates X-ray diffraction spectra (XRPD) of powder rifaximin τ.

The X-ray powder diffraction (XRPD) pattern of the product is characterized by the same 2θ values of diffraction peaks shown in FIG. 2, and corresponds to the X-ray diffraction pattern of FIG. 1, calculated on the basis of single crystal data of Example 1.

The yield of the preparation was 47.3%.

Example 4

Method of Preparation of Rifaximin τ (III)

After having proceeded as in Example 3, the product was further dried under vacuum, with a vacuum of about $8 \times 10^{-3}$ atm, putting the product on a plate per about 30 minutes at 30° C. and connecting the system to a condenser at temperature of −82° C.

The crystal powder was sieved by means of a 100 μm sieve, thus obtaining a crystal product which, once analyzed by HPLC, gave a rifaximin titre of 87.4%; once analyzed by GC, a DEGME titre of 12.1% was obtained; once analyzed by the Karl Fisher method, a water content of 0.48% was measured. The X-ray powder diffraction (XRPD) pattern of the product corresponds to the X-ray diffraction pattern of FIG. 1, calculated on the basis of single crystal data of Example 1.

Example 5

Method of Preparation of Rifaximin τ (IV)

Amounts of DEGME in a molar ratio of 10:1 relative to rifaximin were added to solid rifaximin. The suspension was stirred at 60° C. for about 2 hours until a clear solution was obtained. The solution was left to cool to room temperature, thus obtaining a precipitate, which was isolated and dried for one night under vacuum at 65° C., thus obtaining a crystal product, which, once analyzed by HPLC, gave a rifaximin titre of 85.4%; once analyzed by GC, it gave a DEGME titre of 14.9%; once analyzed by the Karl Fisher method, a water content of 0.3% was measured. The X-ray powder diffraction (XRPD) pattern corresponds to the X-ray diffraction pattern of FIG. 1, calculated on the basis of single crystal data of Example 1.

The yield of the preparation was 93.7%.

Example 6

Method of Preparation of Rifaximin τ (V)

Amounts of DEGEE in a molar ratio of 10:1 relative to rifaximin were added to solid rifaximin. The suspension was kept under stirring at 60° C. for about 2 hours until a clear solution was obtained. The solution was left to cool to room temperature, thus obtaining a precipitate. An amount of heptane having a volume equivalent to DEGEE was added to the solution.

The product was then isolated and dried for one night under vacuum at 65° C., thus obtaining a crystal product which, once analyzed by HPLC, gave a rifaximin titre of 83.2%; once analyzed by GC it gave a DEGEE titre of 15.9%; once analyzed by the Karl Fisher method, a water content of 0.8% was obtained. The X-ray powder diffraction (XRPD) pattern of the product corresponds to the X-ray diffraction pattern of FIG. 1, calculated on the basis of single crystal data of Example 1.

The yield of the preparation was 74.7%.

Example 7

Stability of Rifaximin τ in Different Humidity Environments a) The rifaximin τ obtained according to Example 1 was exposed at room temperature to a humidity level of 11%, obtained by means of a saturated solution of LiCl, for a period of time of 10 days.

b) Another crystal of rifaximin τ was exposed to a humidity level of 84%, obtained with a supersaturated aqueous solution of KCl for 10 days.

The X-ray powder diffraction (XRPD) patterns of rifaximin τ crystals exposed to different humidity correspond to the X-ray diffraction pattern of FIG. 1, calculated on the basis of single crystal data of Example 1.

Example 8

Determination of Intrinsic Dissolution

The determination of the intrinsic dissolution of the powder, which was obtained according to what is described in Example 5, was carried out according to European Pharmacopeia Ed. 7.0, 2010, 2.9.3, page 256, (the disclosure of which is incorporated herein by reference in its entirety), comparing the new crystal of rifaximin τ and amorphous rifaximin and rifaximin polymorph β.

Table 2 reports the obtained values of intrinsic dissolution.

TABLE 2

| | Amorphous rifaximin | Rifaximin τ | Rifaximin polymorph β |
|---|---|---|---|
| Dissolution mg/min/cm$^2$ | 0.131 | 0.121 | 0.016 |

Under the same experimental conditions, the addition of 0.1 ml and 1.25 ml, respectively, of DEGME to the solution contacting the tablet of amorphous rifaximin does not change the measured value of the dissolved rifaximin.

Example 9

Determination of the Dissolution Rate of Rifaximin τ at Neutral pH

An amount of 500 mg of rifaximin τ, 500 mg of rifaximin polymorph α, and 500 mg of amorphous rifaximin were suspended, respectively, in 750 ml of phosphate buffer at pH 6.8 at a temperature of 30±0.5° C. The solutions were stirred for 120 minutes at a stirring rate of 250 rpm. Samples with equal volume were taken at fixed time intervals, filtered and analyzed by spectrophotometer at a wavelength of 430 nm. The rifaximin concentration in the samples was calculated compared to a solution having a known concentration.

The values obtained are reported in Table 3.

TABLE 3

| | Concentration (μg/ml) | | |
|---|---|---|---|
| Time (min) | Rifaximin τ | Amorphous rifaximin | Rifaximin α |
| 5 | 21.68 | 14.4 | 1.05 |
| 15 | 57.68 | 44.0 | 3.26 |
| 30 | 90.54 | 28.7 | 4.23 |
| 60 | 43.14 | 11.0 | 4.12 |
| 120 | 14.93 | 9.1 | 3.89 |

Example 10

Preparation of Pharmaceutical Compositions in the Form of Tablets Comprising Rifaximin τ (Composition A)

An amount of 2340 mg crystal powder rifaximin τ obtained from Example 5 was mixed with starch glycolate, glycerol distearate, talc and microcrystalline cellulose. The mixture was stirred for 30 minutes in a V-mixer and then compacted to obtain granules. The sieved granules were then mixed with extragranular agents: glyceryl palmitostearate, talc, microcrystalline cellulose, silica and the homogeneous mixture compressed to obtain the solid form. The tablets were then coated with a film coating comprising hydroxypropyl methylcellulose, titanium dioxide, sodium edetate and iron oxide.

The unitary composition of the tablets is reported in Table 4.

TABLE 4

| Component | Amount (mg) | Percentage (w/w) Component (%) |
|---|---|---|
| Rifaximin τ | 234.00 | 60 |
| Sodium starch glycolate | 15.00 | 3.8 |
| Glyceryl stearate | 18.00 | 4.6 |
| Colloidal silica | 1.00 | 0.1 |
| Talc | 1.00 | 0.1 |
| Microcrystalline cellulose | 115.00 | 29.3 |
| Hydroxypropyl methylcellulose | 5.48 | 1.4 |
| Titanium dioxide | 1.50 | 3.8 |
| EDTA | 0.02 | 0.005 |
| Propylene Glycol | 0.50 | 0.12 |
| Iron oxide E-172 | 0.5 | 0.12 |

Example 11

Preparation of Pharmaceutical Compositions in the Form of Tablets Comprising Rifaximin τ (Composition B)

An amount of 2340 mg crystal powder rifaximin τ obtained from Example 5 was mixed in a mixer with microcrystalline cellulose, pre-gelatinized starch, talc and magnesium stearate for 20 minutes at 16 rpm. The mixture was then compressed by means of a punch to obtain the tablets. The tablets were then coated. The unitary composition of the tablet is reported in Table 5.

TABLE 5

| Component | Amount (mg) | Percentage (w/w) Component (%) |
|---|---|---|
| Rifaximin τ | 234.00 | 28 |
| Microcrystalline cellulose | 283.25 | 33.6 |
| Pre-gelatinized starch | 280.00 | 33.2 |
| Colloidal silica | 0.8 | 0.95 |
| Talc | 1.00 | 0.12 |
| Magnesium stearate | 0.80 | 0.95 |
| Film coating (titanium dioxide, talc, polyvinyl alcohol, propylene glycol, azorubine, indigotine) | 43.00 | 5.1 |

Example 12

Preparation of Pharmaceutical Compositions in the Form of Tablets Comprising Rifaximin τ (Composition C)

An amount of 2340 mg rifaximin τ, prepared according to Example 5, was mixed in a V-mixer with microcrystalline cellulose, glyceryl palmitostearate, talc and sodium starch glycolate. The homogenous mixture was dry granulated with 3.15 and 1.45 mm meshes, and the granules were mixed with extragranular excipients formed by microcrystalline cellulose, glyceryl palmitostearate, talc and anhydrous colloidal silica. The mixture was stirred for 20 minutes at 16 rpm and then compressed. The tablets obtained were coated with a film coating. The film coating suspended in an aqueous solution was sprayed on the tablets at a temperature of 45° C. The unitary composition of the obtained tablets is reported in Table 6.

TABLE 6

| Component | Amount (mg) | Percentage (w/w) Component (%) |
|---|---|---|
| GRANULE | | |
| Rifaximin τ | 234.00 | 40.6 |
| Glyceryl palmitostearate | 70.00 | 12.5 |
| Talc | 3.75 | 0.6 |
| Microcrystalline cellulose | 100.00 | 17.3 |
| Sodium starch glycolate | 87.7 | 15.2 |
| EXTRA GRANULAR | | |
| Microcrystalline cellulose | 43.5 | 7.6 |
| Glyceryl palmitostearate | 9.00 | 1.6 |
| Talc | 0.6 | 0.1 |
| Anhydrous colloidal silica | 1.6 | 0.2 |
| Film coating (hydroxypropyl methylcellulose, titanium dioxide, talc, iron oxide, sodium edetate) | 25 | 4.3 |

Example 13

Preparation of Pharmaceutical Compositions in the Form of Tablets Comprising Controlled Release Rifaximin τ

An amount quantity of 2340 mg rifaximin τ obtained according to Example 5 was mixed in a V-mixer with microcrystalline cellulose, glyceryl palmitostearate, talc and sodium starch glycolate. The mixture was then granulated by means of a dry granulation process with 3.15 and 1.45 mm meshes. The granules were then mixed with extragranular excipients: microcrystalline cellulose, glyceryl palmitostearate, talc and anhydrous colloidal silica. The mixture was compressed and the cores obtained were then coated with a coating formed by copolymer of methacrylic acid and ethyl acrylate (Eudargit L30 D-55), triethyl citrate, polysorbate 80, glyceryl monostearate suspended in an aqueous solution. The coating solution was then sprayed on the rifaximin cores, pre-heated at 45° C. The unitary composition of the rifaximin τ tablet is reported in Table 7.

TABLE 7

| Component | Amount (mg) | Percentage (w/w) Component (%) |
|---|---|---|
| GRANULE | | |
| Rifaximin τ | 234.00 | 38.4 |
| Glyceryl palmitostearate | 70.00 | 11.5 |
| Talc | 3.75 | 5.7 |
| Microcrystalline cellulose | 100.00 | 16.4 |
| Sodium starch glycolate | 87.7 | 14.4 |
| EXTRA GRANULAR | | |
| Microcrystalline cellulose | 43.5 | 7.3 |
| Glyceryl palmitostearate | 9.00 | 1.5 |
| Talc | 0.6 | 0.9 |
| Anhydrous colloidal silica | 1.6 | 0.3 |
| Film coating: copolymer of methacrylic acid—ethyl acrylate (Eudargit L30D-55) triethyl citrate, polysorbate 80, glyceryl monostearate, water) | 60.1 | 9.9 |

Example 14

Preparation of Pharmaceutical Compositions in the Form of Sachets Comprising Rifaximin τ in Controlled Release Granules In a fluidized bed apparatus, 468 g of rifaximin τ obtained according to Example 5 have been charged with 2.5 g of colloidal silica. At the same time, in a mixer under stirring, a suspension was prepared with 267.3 g copolymer methacrylic acid ethyl acrylate (Kollicoat® MAE100P), 40.1 g propylene glycol, 71 g talc and 18 g titanium dioxide in 1385 g demineralised water. The suspension was charged in the fluidized bed apparatus and nebulised on the rifaximin granules by applying an incoming air flow of 15 m³/h at a temperature of 65° C. The gastroresistant granules obtained were then dried at a temperature of 75° C. for 1 hour.

Colloidal silica, aspartame, sorbitol and cherry flavour were then added to the gastroresistant granules of rifaximin τ. The unitary composition of the sachet corresponding to 400 mg of rifaximin is reported in Table 8.

TABLE 8

| Component | Sachet (mg) | Percentage (w/w) Component (%) |
|---|---|---|
| Rifaximin τ | 468 | 11 |
| Anhydrous colloidal silica | 12.5 | 0.3 |
| Copolymer of methacrylic acid ethyl acrylate (Kollicoat® MAE100P) | 276.3 | 6.9 |
| Aspartame | 20 | 0.5 |
| Propylene glycol | 40.1 | 1.0 |
| Titanium dioxide | 18 | 0.45 |
| Talc | 71.3 | 1.78 |
| Aspartame | 20.0 | 0.5 |

TABLE 8-continued

| Component | Sachet (mg) | Percentage (w/w) Component (%) |
|---|---|---|
| Cherry flavour | 250.0 | 6.2 |
| Sorbitol | 2823.8 | 70.6 |
| TOT (mg) | 4000 | |

Example 15

Determination of the Dissolution of Tablets Comprising Rifaximin τ

The determination of dissolution of rifaximin tablets was executed according to European Pharmacopeia ED. 8.0; 2.9.3, page 288, 2014. A tablet of Normix® comprising 200 mg rifaximin polymorph α was compared to a tablet comprising rifaximin τ, prepared according to Example 10, and to a tablet comprising amorphous rifaximin. The amorphous rifaximin tablets were prepared under the same conditions described in Example 3, with the only exception that amorphous rifaximin was used instead of rifaximin τ

The tablets, comprising rifaximin α, rifaximin τ and amorphous rifaximin, were placed in 1 liter phosphate buffer at pH 7.4 under stirring at 100 rpm at 37° C., respectively, and at given intervals of time, samples of the solution were taken. The rifaximin concentrations were determined by spectrophotometric analysis at 239 nm and compared to a standard solution of rifaximin. The test was repeated with another series of tablets.

Table 9 reports the average concentrations of rifaximin obtained in these two tests.

TABLE 9

| Time (min) | Composition Example 9 (Tablets Rifaximin τ) % Rifaximin (w/w) | Normix ® (Tablets Rifaximin polymorph α) % Rifaximin (w/w) | Tablets amorphous rifaximin % Rifaximin (w/w) |
|---|---|---|---|
| 0 | | 0.0 | 0.0 |
| 15 | 6.0 | 2.5 | 4.1 |
| 30 | 11.5 | 2.8 | 9.3 |
| 45 | 17.1 | 2.8 | 12.5 |
| 60 | 16.6 | 3.1 | 17.0 |
| 90 | 18.3 | 3.2 | 19.4 |
| 120 | 27.1 | 3.1 | 23.0 |
| 180 | 22.4 | 2.7 | 27.2 |

Example 16

PK Study on Dogs Using Rifaximin Prepared by Spray Drying

A bioavailability study of rifaximin τ in comparison with rifaximin amorphous and rifaximin polymorph alpha has been carried out on 4 Beagle male dogs, by feeding them a dose of 100 mg/kg of one of the polymorphs or amorphous form. Each animal received a single oral capsule of rifaximin τ, amorphous rifaximin, and rifaximin α with a washout period of seven days between the administration of each form to the same animal. Doses were administered with a size 13 gelatine capsule followed by 10 ml of drinking water.

Blood was taken at 6 time points up to 24 hours post dose and it was collected into tubes containing lithium heparin anticoagulant.

The plasma has been assayed for rifaximin on the validated LC-MS/MS (Liquid Chromatography-Mass Spectrometry/Mass Spectrometry) method and the maximum plasma concentration observed ($C_{max}$), the time to reach the ($C_{max}$), (tmax), and the area under the concentration-time curve (AUC) have been calculated.

Rifaximin was observed in the plasma of all dogs dosed with 100 mg/kg in a time between 1 hours and 5 hours after dosing and, after 1 hour, rifaximin values were detectable in all animals. Table 10 reports the pharmacokinetic parameters.

TABLE 10

| Rifaximin form | Cmax (ng/ml) | tmax (h) | AUC $_{0-8h}$ (ng•h/ml) | AUC $_{0-tlast}$ (ng•h/ml) |
|---|---|---|---|---|
| τ | 15.70 ± 18.63 | 5 | 19.93 ± 10.25 | 150.54 ± 172.55 |
| Amorphous | 279.79 ± 378.41 | 3 | 1318.02 ± 1975.04 | 2337.16 ± 3223.76 |
| α | 2.84 ± 1.26 | 1 | 7.20 ± 4.00 | 16.86 ± 13.99 |

Cmax: maximum observed plasma concentration;

tmax: time from administration to obtain $C_{max}$ (expressed as median values);

$AUC_{0-8\ h}$: Area under the concentration-time curve from time 0 h (first experimental point) up to 8 hours);

$AUC_{0-tlast}$: Area under the concentration-time curve from time 0 h (first experimental point) up to last quantifiable concentration.

The Examples set forth above are provided to give those of ordinary skill in the art a complete disclosure and description of how to make and use the embodiments of rifaximin τ, compositions, systems and methods of the disclosure, and are not intended to limit the scope of what the inventors regard as their disclosure. All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed Thus, it should be understood that although the disclosure has been specifically disclosed by embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified can be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein can be excluded from a claim of this disclosure. The disclosure illustratively described herein suitably can be practiced in the absence of any element or elements, limitation or limitations which is not specifically disclosed herein.

A number of embodiments of the disclosure have been described. The specific embodiments provided herein are examples of useful embodiments of the invention and it will be apparent to one skilled in the art that the disclosure can be carried out using a large number of variations of the devices, device components, methods steps set forth in the present description. As will be obvious to one of skill in the art, methods and devices useful for the present methods can include a large number of optional composition and processing elements and steps.

In particular, it will be understood that various modifications can be made without departing from the spirit and scope of the present disclosure. Accordingly, other embodiments are within the scope of the following claims.

The invention claimed is:

1. A stable diethylene glycol monoethyl ether solvate crystalline form of rifaximin τ, wherein the crystalline form has a tetragonal crystal system, the space group is P41212 and the unit cell parameters are a=b=16.51 (1) Å; c=36,80(1) Å; α=β=γ=90°; V=10027(1) Å$^3$ or by a X-ray diffraction spectra with peaks at values of angles 2θ±0.1° of 5.9°; 9.0°; 12.9°; 15.4°; 18.8°; 22.8° and 23.4°, wherein the stable diethylene glycol monoethyl ether solvate crystalline form of rifaximin τ does not transform into other forms of rifaximin, and wherein the rifaximin τ has a Cmax value from 0 to 35 ng/ml; $AUC_{0-8\,h}$ from 0 to 35 ng·h/ml and $AUC_{0-tlast}$ from 20 to 235 ng·h/ml.

2. A process for producing a stable diethylene glycol monoethyl ether solvate crystalline rifaximin τ comprising:
adding diethylene glycol monoethyl ether to rifaximin, in a molar ratio ranging from 4:1 to about 500:1, at temperatures ranging from room temperature to 100° C. for a duration of time ranging from 5 minutes to 5 hours to provide a rifaximin solution;
cooling the solution to a temperature ranging from room temperature to −20° C.;
filtering the obtained precipitate;
drying the obtained precipitate at a temperature ranging from room temperature to 40° C. under a pressure comprised between ambient pressure and under vacuum, for a duration of time ranging from 5 minutes to 1 day,
wherein before drying, the precipitate is optionally washed with apolar solvent and thereafter lyophilized.

3. A stable diethylene glycol monoethyl ether solvate crystalline form of rifaximin τ, wherein the crystalline form has a tetragonal crystal system, the space group is P41212 and the unit cell parameters are a=b=16.51 (1) Å; c=36,80(1) Å; α=β=γ=90°; V=10027(1) Å$^3$ or by a X-ray diffraction spectra with peaks at values of angles 2θ±0.1° of 5.9°; 9.0°; 12.9°; 15.4°; 18.8°; 22.8° and 23.4°, wherein the stable diethylene glycol monoethyl ether solvate crystalline form of rifaximin τ does not transform into other forms of rifaximin, and wherein the form of rifaximin τ has an intrinsic dissolution value higher than 0.10 mg/min/cm$^2$.

* * * * *